(12) United States Patent
Euliano et al.

(10) Patent No.: US 9,931,251 B2
(45) Date of Patent: Apr. 3, 2018

(54) WETNESS SENSORS, WETNESS MONITORING SYSTEM, AND RELATED METHODS

(75) Inventors: Neil Euliano, Newberry, FL (US); Glen Flores, Newberry, FL (US); Jerry Yachabach, Gainesville, FL (US); Eric Buffkin, Newberry, FL (US)

(73) Assignee: etectRx Inc., Gainesville, FL (US)

( * ) Notice: Subject to any disclaimer, the term of this patent is extended or adjusted under 35 U.S.C. 154(b) by 897 days.

(21) Appl. No.: 14/233,564

(22) PCT Filed: Jul. 20, 2012

(86) PCT No.: PCT/US2012/047712
§ 371 (c)(1),
(2), (4) Date: Feb. 11, 2014

(87) PCT Pub. No.: WO2013/013197
PCT Pub. Date: Jan. 24, 2013

(65) Prior Publication Data
US 2014/0200538 A1   Jul. 17, 2014

Related U.S. Application Data

(60) Provisional application No. 61/512,071, filed on Jul. 27, 2011, provisional application No. 61/509,774, filed on Jul. 20, 2011.

(51) Int. Cl.
*A61F 13/42*   (2006.01)
*G01N 27/00*   (2006.01)
*G01N 27/12*   (2006.01)

(52) U.S. Cl.
CPC ........... *A61F 13/42* (2013.01); *G01N 27/121* (2013.01); *A61F 2013/424* (2013.01)

(58) Field of Classification Search
CPC .................................................. A61F 2013/424
See application file for complete search history.

(56) References Cited

U.S. PATENT DOCUMENTS 4,704,116 A * 11/1987 Enloe ................ A61F 13/49009
604/358
5,959,535 A   9/1999 Remsburg
(Continued)

FOREIGN PATENT DOCUMENTS

WO   WO 2008021462   2/2008
WO   WO2011054045    5/2011

OTHER PUBLICATIONS

European Patent Office: Supplementary European Search Report dated Mar. 31, 2015 for EP 12814716; entire document.
(Continued)

*Primary Examiner* — Paula L Craig
(74) *Attorney, Agent, or Firm* — Bass, Berry & Sims PLC

(57) ABSTRACT

An aspect of the invention is a liquid sensor having a galvanically energizable power source capable of activating a remotely detectable signal in response to liquid. In a preferred embodiment, a liquid sensor includes a plurality of electrodes, a circuit, and a transmitter thereon. The electrodes are coupled to generate electrical power when in contact with liquid. The circuit is electrically connected to the electrodes so as to be activated by the electrical power, detect an electrical parameter of the electrical power, and generate a plurality of data packets indicating a degree of wetness corresponding to the detected electrical parameter. The transmitter is electrically coupled to the circuit to receive the plurality of data packets and transmit representations of the plurality of data packets as electromagnetic signals. Other aspects include a liquid absorbent wetness (Continued)

sensor and a computer-based wetness monitoring system, and method of detecting liquid.

15 Claims, 14 Drawing Sheets

(56) References Cited

U.S. PATENT DOCUMENTS

| | | | |
|---|---|---|---|
| 6,128,298 A * | 10/2000 | Wootton | H04L 12/4604 370/390 |
| 6,300,871 B1 * | 10/2001 | Irwin | G01K 1/024 340/506 |
| 6,433,695 B1 | 8/2002 | Kai | |
| 6,587,457 B1 * | 7/2003 | Mikkonen | H04W 76/04 370/356 |
| 2002/0019615 A1 * | 2/2002 | Roe | A61F 13/42 604/361 |
| 2002/0145525 A1 | 10/2002 | Friedman et al. | |
| 2004/0070510 A1 | 4/2004 | Zhang et al. | |
| 2004/0078219 A1 * | 4/2004 | Kaylor | G06Q 50/22 705/2 |
| 2004/0230172 A1 * | 11/2004 | Shapira | A61F 13/42 604/361 |
| 2007/0049881 A1 * | 3/2007 | Ales, III | A61F 13/42 604/361 |
| 2007/0255242 A1 * | 11/2007 | Ales, III | A61F 13/42 604/361 |
| 2007/0270774 A1 * | 11/2007 | Bergman | A61F 13/42 604/361 |
| 2008/0058740 A1 * | 3/2008 | Sullivan | A61F 13/42 604/361 |
| 2008/0058742 A1 * | 3/2008 | Ales | A61F 13/42 604/361 |
| 2008/0278337 A1 | 11/2008 | Huang | |
| 2009/0005748 A1 * | 1/2009 | Ales | A61F 13/42 604/361 |
| 2009/0207894 A1 * | 8/2009 | Nefedov | H04W 56/002 375/219 |
| 2009/0302870 A1 * | 12/2009 | Paterson | A01G 25/167 324/670 |
| 2009/0315720 A1 | 12/2009 | Clement et al. | |
| 2009/0322543 A1 * | 12/2009 | Crnkovich | A61F 13/42 340/604 |
| 2009/0326417 A1 * | 12/2009 | Ales, III et al. | A61F 13/42 600/584 |
| 2010/0254311 A1 * | 10/2010 | Simeone | H03L 7/08 370/328 |
| 2012/0016322 A1 * | 1/2012 | Coulthard | A61F 13/0216 604/319 |
| 2014/0336597 A1 * | 11/2014 | Coulthard | A61F 13/0216 604/318 |

OTHER PUBLICATIONS

International Search Report for PCT/US2012/047712 dated Dec. 18, 2012.

* cited by examiner

WETNESS SENSORS, WETNESS MONITORING SYSTEM, AND RELATED METHODS

CROSS-REFERENCE TO RELATED APPLICATIONS

This is a national stage application of International Application No. PCT/US2012/047712, filed Jul. 20, 2012 and titled "Wetness Sensors, Wetness Monitoring System, and Related Methods, which claims priority to U.S. provisional Application No. 61/509,774, filed Jul. 20, 2011 and titled "A Self-Powered Disposable Wetness Sensor and Response System and Related Methods" and U.S. provisional Application No. 61/512,071, filed Jul. 27, 2011 and titled "A Self-Powered Disposable Wetness Sensor and Response System and Related Methods," which are hereby incorporated by reference in their entireties.

FIELD OF THE INVENTION

This invention relates to liquid sensors capable of transmitting remotely detectable signals. More particularly, it relates to liquid sensors with improved signal transmission properties and improved liquid flow management properties.

BACKGROUND

Enuresis, or urinary incontinence (UI), is a health condition affecting many individuals. It is the leading cause of patient admission to a long-term care facility. UI can lead to a variety of medical problems that dramatically increase the cost of care. As a result of prolonged exposure to moisture from UI, perianal skin damage occurs and can progress rapidly to ulceration and secondary infection, including bacterial and yeast infections that increase discomfort and treatment costs. The standard of care required in most long-term care facilities is to check each patient at least every two hours and change them when needed. While this practice ensures a patient should go no longer than two hours without attention, it still leaves as much as a two hour window of wetness exposure should the patient wet shortly following an initial check, putting patients at significant risk of skin breakdown and disrupted sleep during the night. This method also requires staff to waste time checking patients who do not need assistance.

SUMMARY

Although many liquid detecting sensors capable of remotely alerting a caregiver, via radio frequency signals, when a wetness event occurs are known, many of them suffer from drawbacks related to the way the signals are transmitted between the sensors and detectors and the way liquid is transported to the sensor. They also do not provide the ability to determine the degree of wetness or the type of liquid in proximity to the sensor.

The inventors have devised a self-powered powered wetness sensor that uses the liquid to power the sensor's electronics. The sensor's electronics are also configured to include representations of these electrical parameters in the data transmission. Because the electrical parameters vary depending on the degree of wetness and/or type of liquid, the sensors are able to provide this valuable information.

In a preferred embodiment of the sensor, these advantages are achieved by providing a sensor comprising a substrate having a plurality of electrodes, a circuit, and a transmitter thereon. The plurality of electrodes are coupled to generate electrical power when in contact with liquid. The circuit is electrically connected to the electrodes so as to be activated by the electrical power, detect an electrical parameter of the electrical power, and generate a plurality of data packets indicating a degree of wetness corresponding to the detected electrical parameter. The transmitter is electrically coupled to the circuit to receive the plurality of data packets and transmit representations of the plurality of data packets as electromagnetic signals.

Another aspect of the invention is a liquid absorbent wetness sensor that includes one or more of the sensors placed between a plurality of layers of material that receive liquid discharge, such as urine, from a wearer. A preferred embodiment of the liquid absorbent wetness sensor comprises a liquid transport layer positionable next to the skin of a wearer and capable of transporting a volume of liquid discharged by the wearer away from the wearer's skin; a liquid absorbent layer that receives the transported liquid; and a liquid sensor in liquid communication with the liquid absorbent layer. The liquid sensor comprises a galvanically energizable power source capable of activating a remotely detectable signal in response to liquid in the liquid absorbent layer. A liquid management layer is positioned between the liquid transport layer and liquid absorbent layer. The liquid management layer comprises a material that retards liquid flow between the liquid transport layer and liquid absorbent layer so as to prevent the sensor from being energized until the volume of liquid is large enough to flow to the liquid absorbent layer and energize the power source. Here, the liquid management layer is particularly advantageous as it prevents the sensor from being activated unless a substantial wetness event occurs.

In yet another aspect of the invention, the sensor is included in a wetness monitoring system in which one or more transceivers are adapted to receive the plurality of data packets and communicate data over a communication network to an electronic database. The electronic database forms part of a control computer system that can alert a monitoring agent, such as a caregiver, if wetness is sensed. Thereby, allowing the monitoring agent to quickly address the issue.

In a method aspect of the invention, a preferred method of detecting liquid comprises detecting the presence of liquid in proximity to a sensor, the sensor having a substrate with a plurality of electrodes, a circuit, and a transmitter positioned thereon. The electrodes are coupled to generate electrical power when in contact with liquid. The circuit is electrically connected to the electrodes so as to be activated by the electrical power, detect an electrical parameter of the electrical power, and generate a plurality of data packets indicating a degree of wetness corresponding to the detected electrical parameter. The method further comprises receiving a transmitted signal from the sensor, the signal including representations of the plurality of data packets. Other features of the include determining an amount of liquid in proximity to the electrodes by correlating the detected electrical parameter with a wetness value and/or determining a type of liquid in proximity to the electrodes by correlating the detected electrical parameter with a liquid type.

These and other aspects, embodiments, and advantages of the invention will be better understood by viewing the drawings and referring to the following discussion.

DETAILED DESCRIPTION OF PREFERRED EMBODIMENTS

Figure 1:
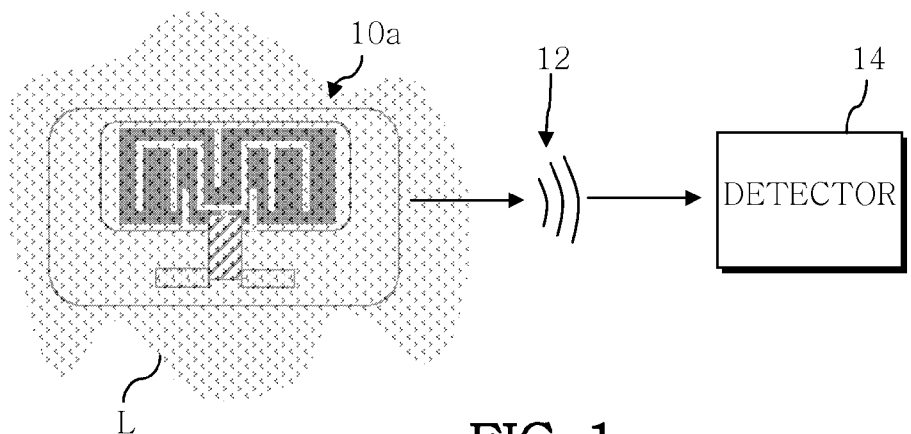
FIG. 1 is a diagram of a first embodiment of wetness sensor in combination with a detector in accordance with an aspect of the invention.

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein. Rather, these embodiments are provided so that this disclosure will convey preferred embodiments of the invention to those skilled in the art.

Before describing the specific aspects and preferred embodiments of the invention in detail, some of the general principles related to the invention are first discussed. A particularly important aspect of the invention is a compact self-powered wetness sensor that may be incorporated into an insert that can be placed inside undergarments such as diapers or briefs to detect wetness therein. The sensor may alternatively be integrated with the undergarment.

In an institutional setting, such as a hospital or convalescent home, the sensor may be attached to patients who suffer from incontinence so that wet diapers, for example, can quickly be addressed by the patients' caregivers. In such settings, an electronic transceiver may be assigned to each sensor being monitored or to a specific location or room. The transceiver contains wireless reception and transmission electronics and is battery powered. The transceiver may be placed remote from the patient or attached to the patient. If the transceiver is attached to the patient, it may be desirable to include a temperature sensor, an accelerometer, a GPS receiver or other geographic location unit to detect the patient's movement and orientation. A single transceiver can preferably communicate with multiple sensors.

The transceiver may also communicate with a computer database via standard wireless protocol and identify its location and item being monitored. The computer system associated with the database acknowledges the transmission and establishes or continues a data file dedicated to that item. The data file includes each transmission's purpose plus the time and date of the transmission. Examples of "transmission purposes" include but are not limited to: sensor has been installed, low receiver battery, accelerometer inactivity, excessive or unexpected accelerometer movement, degree of wetness, "wetness threshold reached" alert, final transmission from a sensor, initial transmission from a sensor, patient location information, movement outside allowed range, and/or patient requires assistance. This information may then be made available for review electronically by any device with authorization for access to that data.

When the item being monitored experiences a liquid insult, the sensors' galvanic cell is activated by the liquid, thereby providing power to the sensor's electronics. After a delay for sensor stabilization and power integration, the sensor begins transmitting data packets at timed intervals proportional to the wetness being sensed or transmits information about the wetness-dependent analog output of the galvanic cell, including but not limited to voltage, amperage, impedance, or capacitance. The data bursts may include a sensor identification code when applicable. The transceiver previously assigned to this sensor receives the data burst, identifies the sensor, initiates the local data table, and records the actual first moment of liquid detection in the database.

The transceiver then attempts to relay this information wirelessly to the database assigned to this item. If the transceiver is not within range of a communications network, it will periodically resend the data until an acknowledgement is received from the computer system. New event data will cause the transceiver to transmit additional data. The data may include the amount of fluid leaked, the general type of fluid leaked, and the number of incidences.

Meanwhile, the sensor continues to periodically send data packets, repeating the sensor wetness information. Several methods of sending information from the sensor are feasible. In one embodiment, the information related to the sensor is transmitted via inter-pulse timing. The pulse rate will be faster when more liquid is detected. For example, if the sensor experiences additional liquid insult, the period between bursts is reduced and the transceiver records this as an additional wetness event. The transceiver then transmits this new data to the database. In another embodiment, the analog value corresponding to the degree of wetness received from the sensor is transmitted digitally to the transceiver. Many different protocols or transmission methods are possible between the sensor and transceiver. The sensor transmits data via RF transmission or fluid conduction. The conduction mechanism operates through the use of small amplitude electrical bursts that can be read by the detector with conductive pads in contact with the same fluid as the sensor.

Since the transmitted information is typically very small, it can be transmitted very rapidly, for example in microseconds. In one embodiment, multiple sensors communicate simultaneously with the use of communications slots through an anti-collision protocol. The transceiver transmits a clock signal with periodic information indicating the start of the first slot. Each sensor that detects this timing information randomly selects a slot and communicates its information during this time period. Since the number of slots can be very large (easily 1000 while maintaining efficient communication throughput), the random chance of any two sensors selecting the same slot is essentially zero. When communication is properly received by the receiver, it can send information to the sensor indicating that the information was received properly. If the sensor does not receive this handshake, the sensor may be colliding with another sensor and can randomly select another slot. As known in the art, many other methods of using two-way communication to allow communication of multiple senders of information are possible.

When integrate and fire communication is utilized, the system leverages the small burst size relative to the total time available to transmit. In a one-way communication scenario, the sensors send data packets at random start times and the receiver partitions the pulse trains with various algorithms. One such suitable algorithm called "independent component analysis" looks for patterns in the repetitive nature of the signals and finds the independent sources without knowledge of the number of sources or the identity of the sources. With two way communication and integrate and fire communication, the data packets can be synchronized to slots defined by the transceiver's clock signal. Data packets are integrated until a threshold is reached and then the transmission occurs only when its assigned (randomly or by the master receiver) slot arrives next.

The sensor preferably has a generally planar form factor, with small 3D features defining the sensor circuitry, such as metallization areas, an electronic bursting circuit, various coatings, and the like. The generally planar geometry allows the system to be used in a number of applications, such as those described herein. The sensor may be fully three-dimensional to help facilitate signal directionality, allow for fluid management structures, or allow for more appropriate placement.

The various aspects and embodiments of the invention have many advantages. Some but not all of those advantages are now described. Not every aspect and/or embodiment of the invention is require to achieve all of these advantages.

The wetness sensor itself has many advantages. Because it is only activated through liquid contact it has a nearly unlimited shelf life. Some embodiments of the sensor are compact, flexible, and disposable.

Liquid flow control techniques used in certain embodiments of the sensor assemblies use a unique combination of standard diaper materials to direct the flow of liquid to or from the sensor as needed. This allows large areas to be monitored with the minimum number of sensors.

Integrate and fire RF technology allows for battery-less operation (energy harvesting) while allowing enhanced range of detection. It also provides for enhanced data transmission by incorporating information in the pulse timing of the data stream.

The cost of making the sensors is exceptionally low, which makes the sensors more amenable to being disposed of after user.

A more detailed description of these aspects and embodiments of the invention are now discussed.

A. Wetness Sensor

Referring initially to FIG. 1, a self-powered wetness sensor 10a in accordance with an embodiment of the invention self-generates the electrical power needed to operate its circuitry when it comes into contact with a conductive liquid L. The sensor's circuitry uses this power to transmit an electromagnetic signal 12 to a remote electromagnetic detector 14. The signal 12 includes information about the wetness event that generated the conductive liquid L. Additional details of the sensor 10a and an alternate embodiment thereof are now described in connection with FIGS. 2-5.

Figure 2:
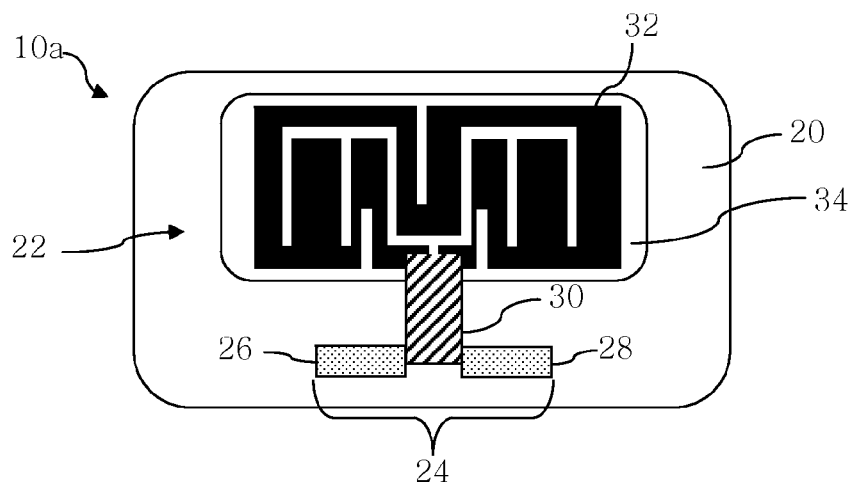
FIG. 2 is a top plan view of the first embodiment of the wetness sensor in accordance with an aspect of the invention.
Figure 3:
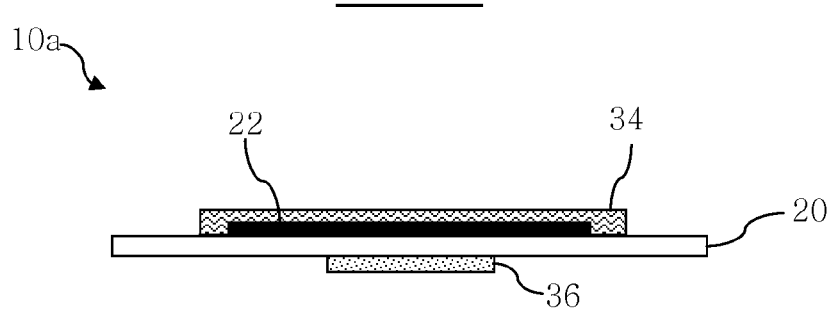
FIG. 3 is a side elevation view of the wetness sensor of FIG. 2.

The wetness sensor 10a embodied in FIGS. 2 and 3, includes a substrate 20 with sensor electronics 22 located thereon. The sensor electronics 22 include a galvanic cell 24 equipped with a first conductive lead 26 and a second conductive lead 28. The conductive leads 26, 28 of the galvanic cell 24 are in electrical contact with an integrated circuit 30, which is in electrical contact with an antenna 32. An electrically insulating layer 34 is placed over the sensor electronics 22, but leaving the galvanic cell 24 exposed. While not always required, an attachment member 36 for attaching the sensor 10a to a desired surface may be placed on the side of the sensor 10a opposite the sensor circuitry 22 as represented in FIG. 2. Suitable attachment members 36 include adhesives, adhesive tapes, hook and loop-type fasteners, or the like.

The sensor 10a may be constructed very small or very large, depending on what is desired. For many applications, it is desirable to use very small sensors having dimensions on the order of centimeters or millimeters. In a preferred embodiment, the sensor 10a is about 2 cm along its length and about 1 mm thick.

Figure 4:
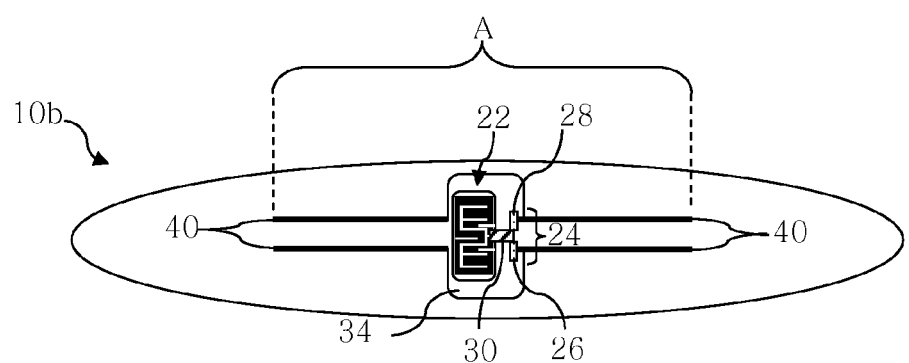
FIG. 4 is a top plan view of a second embodiment of a wetness sensor in accordance with an aspect of the invention.
Figure 5:
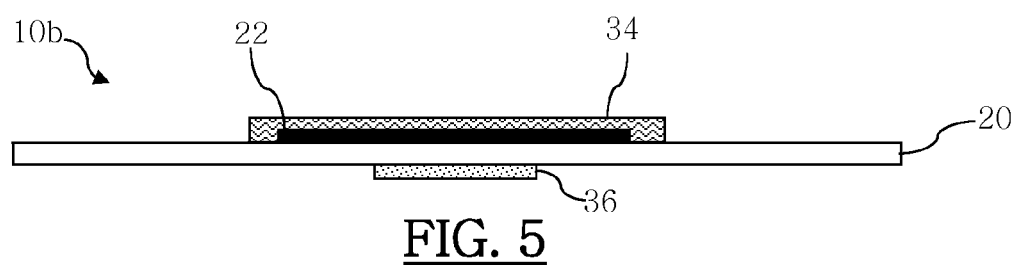
FIG. 5 is a side elevation view of the wetness sensor of FIG. 4.

Referring now to FIGS. 4 and 5, a sensor 10b having an increased wetness detection area A, according to an embodiment of the invention, includes a substrate 20, sensor circuitry 22, galvanic cell 24 equipped with a first conductive lead 26 and a second conductive lead 28, integrated circuit 30, antenna 32, and electrically insulating layer 34; all of which are configured to operate in the same fashion. The substrate 20, however, is elongated to accommodate a plurality of conductive lead extensions 40. The conductive lead extensions 40 are in electrical contact with the leads 26, 28 such that, when the lead extensions 40 come into contact with a conductive liquid, the galvanic cell 24 generates electricity.

The substrate is preferably made of a thin flexible material, including various polymers. Examples of suitable materials include, but are not limited to, polyesters, polyolefins, polyimides, acrylics, vinyls, and papers.

The electrically insulating layer is preferably made of a thin flexible material, including various polymers. Examples of suitable materials include, but are not limited to, ethylcellulose, epoxies, silicone, and PETE (TEFLON).

In either embodiment of the sensor 10a,b The galvanic cell 24 self-powers the sensor 10a,b when it becomes wet with a conductive liquid, which may include bodily liquids such as urine, blood, or any other ion containing liquid, for example. This is because the conductive liquid forms electrical contact between the conductive leads 26,28.

In a preferred embodiment, the galvanic cell 24b creates a measurable analog output such as current, voltage, or resistance in various wetness situations. When wet, the galvanic cell 24 supplies electrical power to the sensor 10a,b. The galvanic cell 24 will begin powering the integrated circuit 30 as soon as it is wetted. This, in turn, operates the antenna 32 which transmits the electromagnetic signal 12 that can be read by the electromagnetic signal detector 14.

The conductive leads 26,28 are preferably made of different metals or compounds having different reduction/oxidation potentials similar to the anode and cathode of a battery. When the conductive leads 26, 28 are placed in a conductive liquid, an electric voltage and current are generated. The materials used to make the leads 26, 28 may be chosen from any number of metals and/or conductive carbon-based inks. Preferred first conductive lead 26/second conductive lead 28 combinations include: carbon-based ink/zinc, silver/zinc, copper/zinc, silver/magnesium, copper/magnesium or the various salts thereof (silver chloride or silver phosphate, for example).

If desired, metals used for the leads 26,28 can be transformed by a number of chemical or physical reactions to produce a new chemical compound or material state/character (phase, crystallinity, surface texture). By way of example, silver may be transformed to silver phosphate by electrostatically applying a positive voltage to a silver film in the presence of phosphate ions. Thus, a silver phosphate cathode may be used with a zinc anode to form a galvanic cell. The new compound yields a change the differential voltage compared to non-transformed electrodes. Magnesium and zinc can be combined by vapor deposition or other methods to create a magnesium/zinc anode. Taking advantage of other changes in the lead 106,108 are also contemplated. These changes include: phase transitions, state transitions, structural changes, and other materials transitions that cause a change in the electrical output of the galvanic cell. Transformation can occur on the anode or cathode of the galvanic cell.

For high peak current loads, additional capacitance may be added to the sensor circuitry 22. The capacitance can be added to the integrated circuit 30 the sensor itself 10a,b, or the substrate 20. For example, the printed tracings between the galvanic cell 24 and the integrated circuit 30 may contain two printed metallic plates separated by a dielectric that produces a capacitance that will store sufficient charge to handle the peak current loads. Other methods of adding capacitance are also possible.

The galvanic cell's 24 source resistance or voltage may be used a gauge of the amount of wetness in the vicinity of the sensor 10a,b. The current draw will begin to pull the galvanic cell 24 voltage below the peak operating voltage in two scenarios: (1) when the galvanic cell 24 is loaded down at its output at the integrated circuit 30, and/or (2) when the amount of conductive liquid is insufficient to maintain the electrochemical reaction between the leads 26,28. Either or both scenarios will yield an output voltage and, therefore, the determined source resistance, that varies with the amount of liquid presented to the sensor 10a,b. The cell voltage is a function of the nature of the ionic fluid and the degree of wetness connecting the leads 26,28. In addition to any instantaneous wetness, by the use of liquid flow control, the amount of liquid connecting the leads 26,28 can be made to dissipate over time. The degree of wetness of the surrounding environment of the galvanic cell 24 can affect the speed at which the liquid dissipates in the immediate area of the galvanic cell 24. As the liquid dissipates, the galvanic cell's 24 internal resistance increases and can be used as an indicator of wetness. The degree of wetness and the dissipation phenomenon are converted to a proportional time interval spacing of transmitted data packets.

The voltage produced by the galvanic cell 24 may also be influenced by the galvanic cell's 24 geometry. For example, elongated parallel cell leads 26,28 produce a real resistance change in the galvanic cell 24 when exposed to the conductive liquid. As the liquid comes into contact with the sensor 10a,b, the leads 26,28 become increasingly wetted and capable of generating current. The current or voltage at a given wetted area can then be measured. The output voltage for the galvanic cell 24 is then measured by the integrated circuit 30.

Accordingly, the galvanic cell's 24 voltage, current, and/or resistance provide valuable data points that can be used to infer the degree of wetness in the vicinity of the sensor 10a,b. In order to be useful, however, these data are preferably transmitted from the antenna 32 to the detector 14. In practice, the integrated circuit 30 transmits this information to the detector via the antenna 32 using data bursts at a given time period. A data packet's characteristics are dependent on the input voltage from the galvanic cell 24. Other suitable methods for communicating this data from the sensor 10a,b to the detector 14 include digital methods and conventional methods that vary frequency or amplitude.

The chemically or physically altered leads 26,28 may also be used to distinguish different conductive liquids. Differing wetness liquids, by their ionic concentration and/or atomic composition, may alter the output electrical characteristic of the galvanic cell 24. For example, the galvanic cell 24 in the presence of urine may produce only 1 V, but in the presence of spilled juice it may produce 1.4 V. Likewise, the current or internal resistance of the galvanic cell 24 may change depending on the type of wetness.

In this context, a particularly advantageous use of the sensor 10a,b is as a diaper wetness sensor. In this case, the galvanic cell 24 may be used to discriminate between urine and spilled beverages and transmit a signal to the detector 14 only in response to urine.

The integrated circuit, 30 measures the voltage across the leads 26,28 and generates a signal 12 that is transmitted to the detector 14 if and/or when the target electronic reading is reached in the vicinity if the wetness source. If the sensor 10a,b is not close enough to the wetness source, the voltage will not change appreciably as no chemical transformation will proceed. Thus, the voltages can be transmitted via the sensor 10a,b to the detector 14 to confirm the that liquid detected is one of concern.

Conventional wetness sensors are typically highly complex when designed for analyte specificity or are too simplistic and therefore not analyte-specific. Material transformation of the leads 26,28 allows for increased specificity, especially for the limited range of chemicals typically found in the human body. Furthermore, many pH sensors, potentiometric sensors, actuating sensors, optical/fluorescent sensors, or otherwise require power to analyze incoming signals. Being a system that requires no input energy (and can in fact power a cell in itself), our materials transformation wetness sensor keeps parts and design complexity to a minimum. For additional capabilities, sensors that require only microamps of current are also suitable, as they can derive power from the galvanic cell 24a,b.

The sensor 10a,b may store energy that allows it to use the galvanic cell 24 in a manner that measures resistance or capacitance or test various species using simple coatings. The sensor 10a,b may be coated with one or more coatings selective to ions, molecules, electropotential, polarity, charge, or solvents. In an exemplary embodiment, a polyurethane coating that is selective for chloride ions is coated over the leads 26,28 allowing the sensor 10a,b to be used for checking for the presence of salts such as those found in incontinence events or for impurities in drinking water.

Urease may be used as an analyte-selective electrochemical sensor to produce an added electrical impulse in the presence of the urea in urine when used in conjunction with various field effect transistors (FETs).

In yet another exemplary embodiment, the leads 26,28 are coated with a material that only dissolves in the presence of certain desired liquids.

Figure 25:
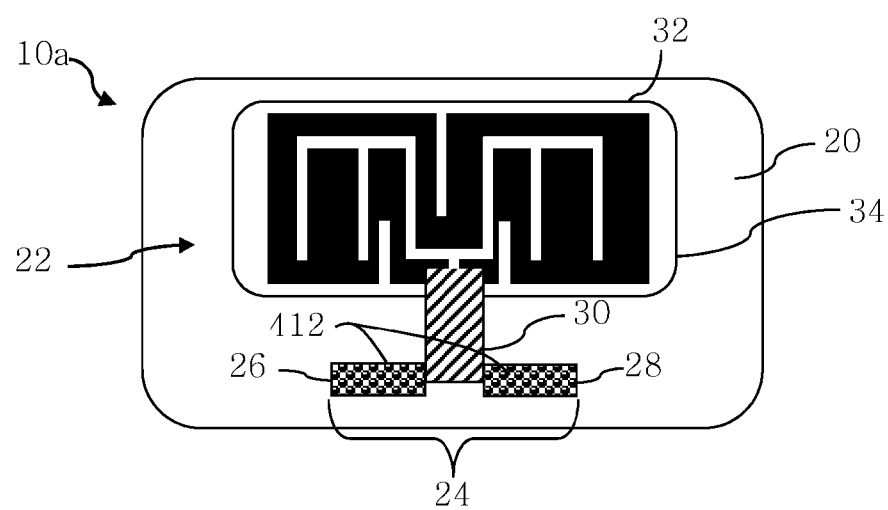
FIG. 25. is a top plan view of the wetness sensor embodiment of FIGS. 2 and 3, showing coated leads.

Referring to FIG. 25, the sensor 10a includes a coating 412 placed over the leads 26,28.

The voltage output of the galvanic cell 24 can be measured by the integrated circuit 30 and transmitted to the detector 14 as part of a data packet that indicates the type of liquid encountered and/or the degree of wetness.

The integrated circuit 30 implements a very low power, low bandwidth communications circuit that requires low voltage (~1 V) and low power (~10 uW). Input power can be supplied by a variety of energy harvesting techniques.

In some instances, the voltage level of the galvanic cell 24 may not have sufficient dynamic range to determine accurate sensor information (e.g. wetness). By placing a resistive load inside or outside the sensor circuitry 22, the voltage level can be modified to provide better information from the sensor 10a,b. In some cases, it may be desirable to toggle the resistive load on and off to allow power to flow freely to the sensor circuitry 22 during normal operation but to add the resistive load only when the voltage level is being measured.

A drawback to using the very small galvanic cells 24 is that there are significant limits to obtaining steady-state voltage and current. To overcome this drawback, an energy harvesting technique, called "integrate and fire" has been chosen by the inventors as the preferred signaling method. Conventional RF output signaling requires significantly more power than a small galvanic cell can generate but the amount of information that must be transmitted can be done so in a very short period of time, typically within microseconds. The design goals met using the integrate and fire technology allow for a 1000 to 1 benefit in transmission burst output power.

The voltage output of the galvanic cell 24 can also be used to directly modulate or modify the signal being transmitted to the detector. In a preferred embodiment, using the "integrate and fire" methodology, the burst rate of the sensor 10a,b is modified by the voltage level of the galvanic cell 24. An analog circuit including resistors, capacitors, and transistors is used to store the electrical power generated by the galvanic cell 24 until a threshold value is met. Once the threshold value is met, the electrical power is released to power the sensor circuitry 22 and thereby transmit the signal burst. The integrate and fire technique facilitates ultra-low power transmission capabilities while allowing valuable information to be incorporated in the configuration of the transmitted data stream. The integrate and fire technique has multiple objectives, including providing a sensor 10a,b having ultralow power consumption, low cost, and a very small form factor.

The "integrate and fire" transmission techniques utilized herein achieves the ultralow power transmission in relatively high RF noise environments. This technique is practical because the amount of data being transmitted is relatively small while the time available to transmit it is relatively long. In practice, the voltage output of the galvanic cell 24 powers the integrated circuit 30 and additionally charges a charge integrating capacitor. While the integrated circuit 30 manages the electrical activity, the integrating capacitor is charging. On command from the integrated circuit 30 when a voltage threshold is reached, the charged capacitor is connected to a voltage multiplying circuit which drives the antenna 32 with an output pulse duration several orders of magnitude shorter than the charge time. The available RF power in the transmitted pulse is a function of the relative duration of the charge time to the discharge time multiplied by the efficiency of the voltage multiplier plus the transmitter circuit.

By monitoring the time duration between pulses, the charge rate of the charge accumulating capacitor can be determined. If the electrochemical cell has a high source impedance, indicative of a low degree of wetness, the capacitor takes longer to charge. The time between succeeding RF transmission bursts therefore is an indication of the degree of wetness the sensor 10a,b is detecting. By utilizing and controlling the time domain as an indication of transmitted analog data, significant improvements in ultralow power transmission in high RF noise environments are achieved.

Because the sensor 10*a,b* can operate at very low power, it may be embedded in host systems for prolonged periods of time until wetness activates the galvanic cell 24, causing the sensor to transmit an RF signal with a range far exceeding that which passive RFID systems can achieve.

A second objective of the integrate and fire concept adopted herein is to control the time interval between the transmission bursts as an indicator of the value of the input signal being monitored.

Differing voltages or current capabilities of the lead-liquid combination produce different signal burst rates. Similarly, different burst lengths, amplitudes, or frequencies can be created based on the voltage or current of the lead-liquid combination. These methods produce a self-powered transmission of the sensor value to an remote detector. These signaling methods are preferably built into the integrated circuit 30. Preferably, the integrated circuit 30 circuits electronics that are printed onto a flexible substrate producing a very small, flexible, and substantially planar sensor transmission system.

An alternative approach to self-powering the sensor 10*a,b* is a battery that can be water-activated and embedded in a RFID tag. An example of such a battery is described in U.S. Pat. No. 5,395,707, which discloses a primary reserve battery useful in sonobuoys on the ocean. The battery uses cuprous iodide as a cathode and magnesium as the anode in an array to provide voltage, amperage, and operational time equivalent to conventional lead chloride batteries. Once the sonobuoy is no longer useful as it deteriorates in the environment, no lead will be presented into the ocean. The structural frame members protect the cuprous iodide which is brittle in a rigid array and provides for proper venting of gas and sludge formation to insure efficient operation of the battery.

Other kinds of batteries activated by other liquids like water can be found in the literature. For instance, U.S. Pat. No. 4,185,143 discloses a water activated battery using a metal/organo-halogen couple wherein the anode and cathode are formed as planar members with a porous insulator sandwiched between. There are provided channels to allow the electrolyte access throughout the cell. The channels may be cut in the cathode or the cathode may be formed as discrete portions of cathode reactant material deposited on a current collector backing plate. The portions of U.S. Pat. Nos. 5,395,707 and 4,185,143 describing their respective batteries is hereby incorporated by reference.

There are also alternate means for sensing the presence of liquid aside from the galvanic cell 24. For example, one or more low power sensors apart from the galvanic cell 24 may be used. A cathode of anode, for example, that is analyte selective, but is not responsible for providing the majority of the power are possible to use.

B. Wetness Sensor Assembly

In yet another aspect of the invention, a sensor 10*a,b* is incorporated into a sensor assembly having components designed to manage the movement of liquid in the vicinity of the sensor 10*a,b*.

Sensor assemblies made in accordance with aspects of the invention employ unique, yet simple, physical mechanisms for liquid management, utilizing inexpensive materials to gauge liquid levels and control liquid flow to the sensor 10*a,b* as desired.

By placing the sensor 10*a,b* in a sensor assembly of the invention, a simple solution to preventing false alarms due to nuisance wetting (sweat, trickles, condensation) is obtained.

The sensor assembly includes a plurality of material layers adapted to control the flow of liquid to the sensor 10*a,b*. The materials may include hydrophilic top layers, acquisition and distribution layers, absorbent layers, and non-absorbent backing layers. The sensor assembly may be made into an insert for a undergarment or diaper or as a feminine hygiene pad. Alternatively, it may be incorporated into the production process of diapers, either within the diaper or extra-diaper, as desired.

The sensor assembly is constructed using manufacturing techniques and layering similar to that used to manufacture feminine hygiene pads.

The material layers may be sheets, films, porous fabrics, coatings, gels, or the like. In one embodiment, two sheets of material comprise the liquid management and absorbent layers are affixed to opposing sides of the sensor. The layer materials may be chosen from any number of materials, including polymers, waxes, gelatins and fibers.

Figure 6:
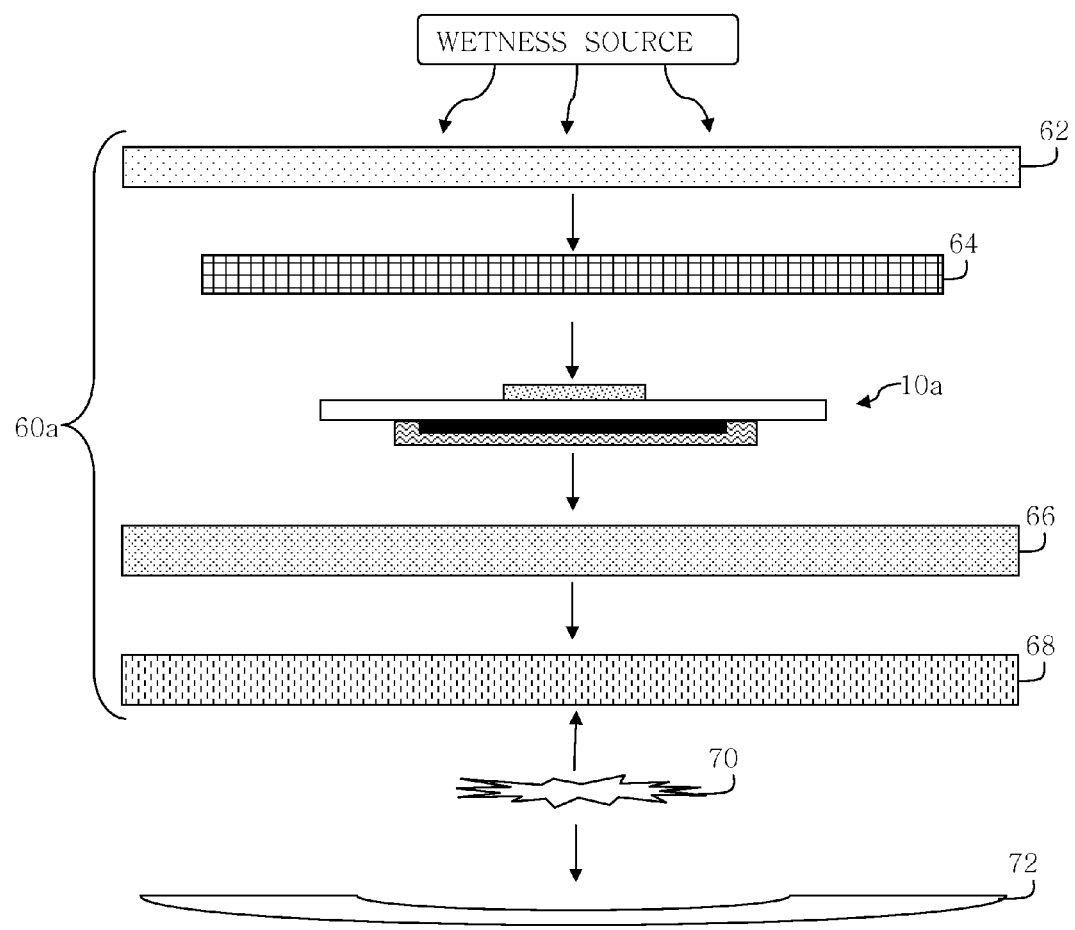
FIG. 6 is an exploded view of a first embodiment of a sensor assembly, highlighting its method of construction in accordance with an aspect of the invention.

Referring to FIG. 6, a sensor assembly 60*a* in accordance with an embodiment of the invention includes a sensor 10*a* located between a plurality of material layers. The arrows indicate the direction of wetness flow towards from the wetness source toward the sensor assembly 60*a*. The sensor assembly 60*a* includes a top layer 62, liquid management layer 64, absorbent layer 66, and bottom layer 68.

In use, the top layer 62 will be placed closest to the wetness source. The top layer 62 is preferably made of spunbond polyester for allowing liquid to pass through to the material layers beneath it while separating conductive liquid, such as urine, from the user's skin. The top layer 62 provides the top surface and overall shape of the sensor assembly 60*a*. The spunbond polyester material is commonly used as the top layer in diapers.

The liquid management layer 64 is particularly advantageous as it is adapted to prevent the sensor 10*a* from being triggered by 'nuisance events' such as moisture, humidity, urine drips, or sweat from the user. The liquid management layer 64 is preferably made of a water impermeable material such polyethylene or similar waterproof polymer. In the embodiment shown in FIG. 6, the liquid management layer 64 is smaller than the top layer 62 and the absorbent layer 68 to allow liquid to move to the absorbent layer 68.

As mentioned above, the liquid management layer allows for greater functionality of the sensor assembly 60*a*. Because it protects the sensor 10*a* from direct wetting, it can allow for prevention of false alarms due to nuisance or small-volume wetness events.

Furthermore, the liquid management layer 64 also provides a degree of control in liquid sensing. In conjunction with the absorbent layer 66, the liquid management layer 64 allows for control over the amount of liquid needed to trigger the sensor 10*a* to send a signal 12 reporting a wetness event. In an embodiment in which the sensor 10*a* is sandwiched between the liquid management 64 and absorbent layers 66, the amount of liquid necessary to trigger the sensor 10*a* to send the signal 12 is related to the size of the liquid management layer 64. A smaller liquid management layer 64 will allow liquid to reach the absorbent layer 66 at a position closer to the sensor 10*a* than would a larger layer.

The liquid management layer 64 may be of a number of shapes, geometries, and patterns that can enhance the degree of liquid sensing control. It can be shaped to help guide liquid towards the sensor 10*a* regardless of the user's spatial orientation. For example, it may have a number of open sections nearer to the sensor to act as an inlet for liquid absorption, especially in cases where the absorbent layer 66*a* might be impeded from distributing liquid to the sensor 10a. Thus, if a liquid insult occurs away from the sensor 10a, especially for male users, the liquid management layer 64 drains the liquid towards the sensor 10a.

The liquid management layer 64 may be composed of semi-permeable materials that can greatly limit liquid flow and prevent or delay the absorbent layer from saturating with nuisance wetness events such as trickles or small volume voiding. Alternatively, it may be a combination of layers of absorbent materials and liquid impermeable materials to absorb wetness but prevent direct wetting of the sensor 10a. The liquid management layer 64 is preferably made of one or more polymers selected from polyesters, polyethylenes, polypropylenes, polystyrenes, acrylates, or other water-impermeable materials.

The size of a particular layer is contingent upon the amount of wetness to be sensed, the wetness area, and the material from which the layer is made. In general, the liquid management layer 64 is either smaller than the absorbent layer 66 but larger than the sensor 10a or has a porous or open structure that directs liquid to wet the absorbent layer 66 at specific sites. Liquid wetted directly atop the liquid management layer 64 traverses the surface of the liquid management layer 64 and wets the underlying absorbent layer 66, which subsequently wets the sensor 10a. The liquid management layer 64 may also be used only to prevent direct wetting of the sensor 10a and liquid, but otherwise allowing the absorbent layer 66 to be wetted first.

The liquid management layer 64 may have holes in it to allow the majority of the conductive liquid to flow through it, essentially leaving only a mesh of material to collect fluids. This prevents fluid from accumulating at the sensor 10a.

The liquid management layer 64 may have fluid wicking arms/threads/tubes that collect fluid from a large area and draw it toward the sensor 10a.

In this embodiment, the sensor 10a is located between the liquid management layer 64 and the absorbent layer 66. The sensor 10a is oriented with the back side of the substrate 20 contacting the liquid management layer 66. The side of the sensor 10a on which the sensor circuitry is located abuts the absorbent layer 66. This orientation allows for the leads 26, 28 to be wetted by conductive liquid in the absorbent layer 66.

In this embodiment, the substrate 20 is preferably less than 200 mm² in area. The leads 26,28 are made, respectively, from silver phosphate and magnesium. The leads 26,28 preferably have an area less than 9 mm² and are less than 0.25 mm thick. The antenna 32 is preferably made from silver particle ink printed onto the polyester substrate.

The absorbent layer 66 is preferably made of a hydrocolloid-type of material that swells when it absorbs water such as the hydrocolloid materials used in conventional diapers. Suitable materials capable of achieving this function include cellulosic materials. The absorbent layer 66 wicks the conductive liquid toward the sensor 10a.

The absorbent layer 66 allows for a wide area of sensing using a single small sensor 10a. The absorbent layer 66 effectively acts to transport liquids from remote areas of the sensor assembly 60a to the sensor 10a. Materials with rapid wicking or capillary properties, such as lateral flow strip material, are ideal for this embodiment. This allows for longer distance sensing than would be normally available.

Dryness sensors can be used in bags that empty rather than fill. The wicking agent can allow continuous transport of liquid in to a reservoir or additional absorbent layer. When liquid is no longer available, the wicking material empties and no longer signals liquid at the site.

The absorbent layer 66 may be made of liquid retaining materials that allow for the collection of small amounts of liquid and moisture over time. The liquid continually migrates towards the sensor 10a as additional liquid is collected. When enough liquid has been collected, the sensor 10a is triggered and a signal 12 is transmitted to the detector 14. Thus, a user whose enuresis is in the form of minor wetting events may also allow a wetness signal to be triggered after sufficient wetting even when no singular wetting event may be sufficient for triggering a signal.

The bottom layer 68 is preferably made of the same material as the top layer 62 and is the same size as the top layer 62. The bottom layer 68 allows liquid to pass through to the undergarment beneath and provides the bottom surface for the sensor assembly 60a. If desired an adhesive 70 may be applied to the bottom layer 68 for affixing the sensor assembly 60 to a undergarment 72 such as a diaper. If the sensor assembly is to be used in conjunction with standard diaper, the bottom layer 68 is preferably made of spun bonded polyester with hydrophilic characteristics. If, however, the sensor assembly 60a is to be used with a standalone liquid absorbing product, such as a undergarment insert, the bottom layer 68 is preferably made of propylene resin without any added surface surfactants. This cloth-like film prevents leakage out of the sensor assembly 60a.

Figure 7:
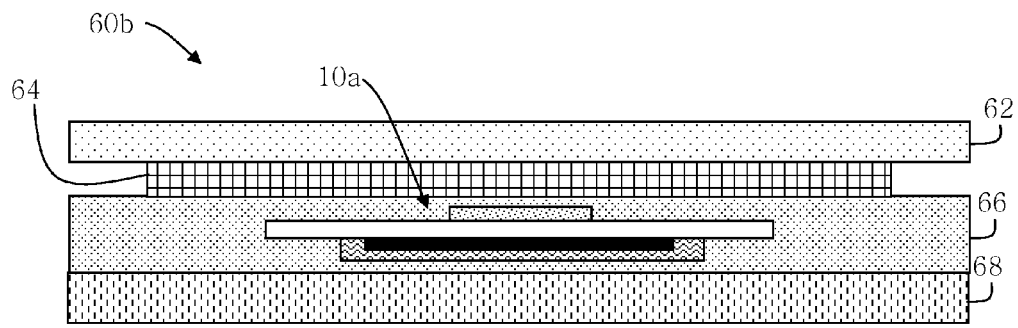
FIG. 7 is a side cross-sectional view of a second embodiment of a sensor assembly in accordance with an aspect of the invention.

Other arrangements of the sensor assembly are also possible. Referring to FIG. 7, in an alternative embodiment of the sensor assembly 60b, the sensor 10a is incorporated into the absorbent layer 66 and the liquid management layer 64 is placed atop the absorbent layer 66b. The bottom layer 68 is located on the side of the absorbent layer 66, that is opposite the liquid management layer 64.

Figure 8:
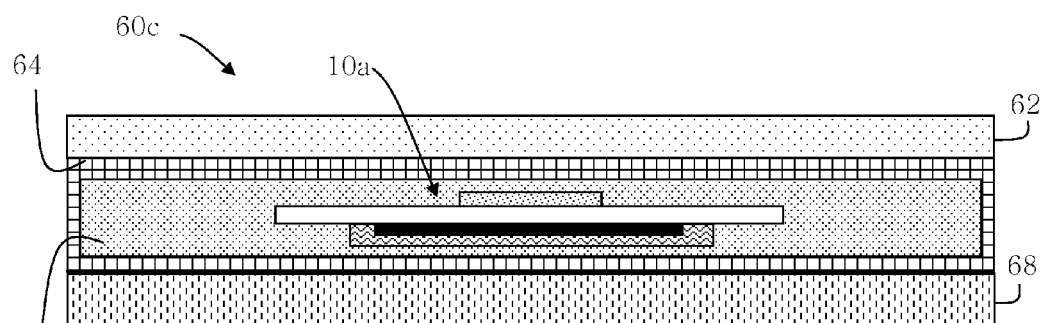
FIG. 8 is a side cross-sectional view of a third embodiment of a sensor assembly in accordance with an aspect of the invention.

Referring to FIG. 8, in another alternative embodiment of a sensor assembly 60c, the liquid management layer 64 encompasses the sensor 10a and absorbent layer 66. In this embodiment, the liquid management layer 64 preferably includes minimally porous, swellable, or slowly degrading/dissolving materials, or any other materials that retard the flow of liquids without completely blocking them. Alternatively, the liquid absorbent layer 66 may encompass the liquid management layer 64 to prevent liquid from pooling over the liquid management layer 64.

Figure 9:
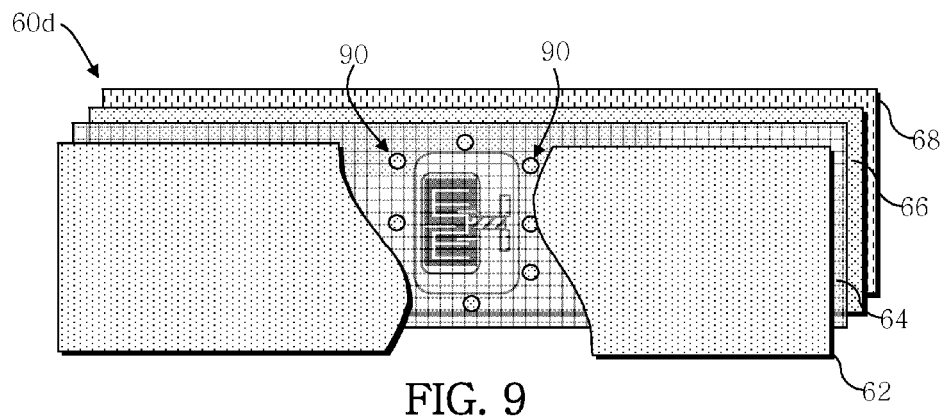
FIG. 9 is a top exploded view of a fourth embodiment of a sensor assembly in accordance with an aspect of the invention, in which the top layer is cut-away to provide a better view of the liquid management layer.
Figure 10:
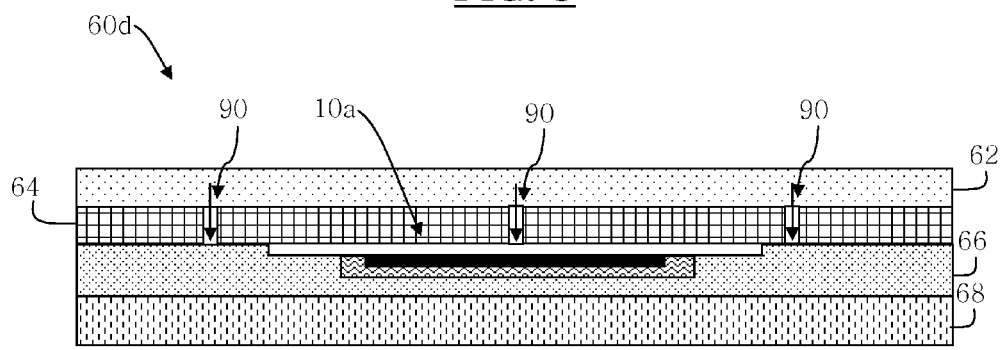
FIG. 10 is a side cross-sectional view of the sensor assembly of FIG. 9.

In yet another preferred embodiment of a sensor assembly 60d shown in FIGS. 9 and 10, the liquid management layer 64 overlaps the absorbent layer 66 but follows its general shape and contour. A plurality of perforations 90 penetrate the liquid management layer 64 for allowing liquid to drain through the liquid management layer 64 towards the absorbent layer 66 in proximity to the sensor 10a. The arrows in the perforations 90 in FIG. 10 illustrate the direction of liquid flow. In FIG. 9, the liquid management layer 64 is shown as being transparent in order to provide an understanding of where the sensor 10a is located.

Figure 11:
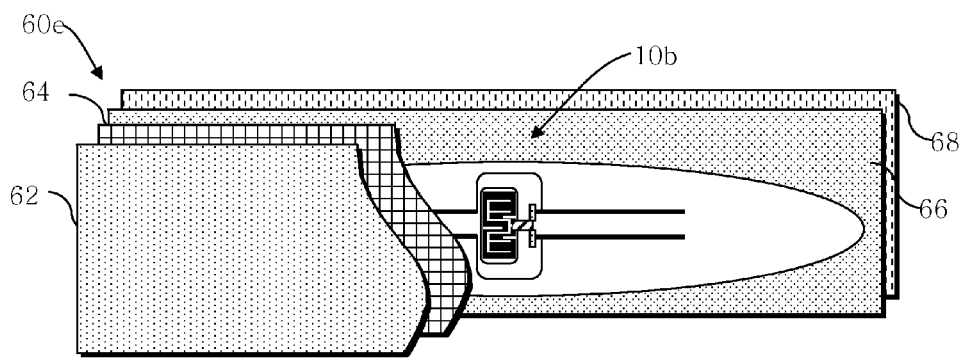
FIG. 11 is a top exploded view of a fifth embodiment of a sensor assembly in accordance with an aspect of the invention, in which the top layer and an acquisition and distribution (ADL) layer are cut-away to provide a better view of the elongated sensor.

The dimensions of the sensor 10a used in the sensor assembly may be adjusted as desired. Referring to FIG. 11, a sensor assembly 60e in accordance with an alternative embodiment of the invention includes the elongated sensor 10b, the top layer 62, liquid management layer 64, absorbent layer 66, and bottom layer 68. This configuration is useful where the wetness area is large and the sensor assembly 60e replaces a feminine hygiene pad or acts as an insert for a female or child's diaper or panty.

Figure 12:
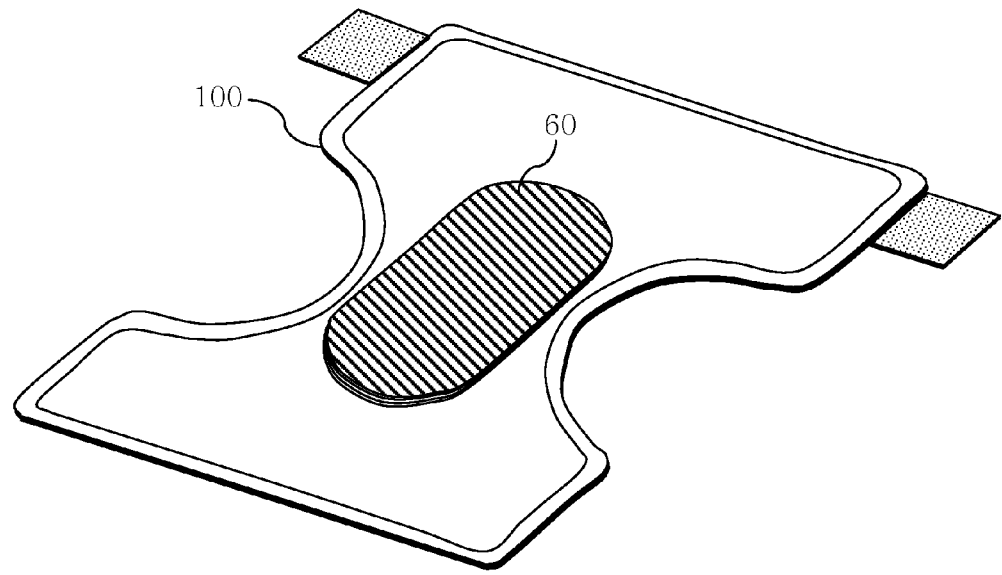
FIG. 12 is a top perspective view of the interior of a diaper having a sensor assembly thereon in accordance with an aspect of the invention.

The various embodiments of the sensor assembly are particularly useful as wetness detecting inserts for undergarments, including adult or baby diapers or briefs. FIG. 12, shows a diaper 100 with a sensor assembly 60, which could be any of the sensor assemblies 60a-f described herein, located in the crotch region thereof on the interior side of the diaper 100. The sensor assembly 60 may be attached to the diaper 100 using an attachment mechanism 36 as described previously.

Figure 13:
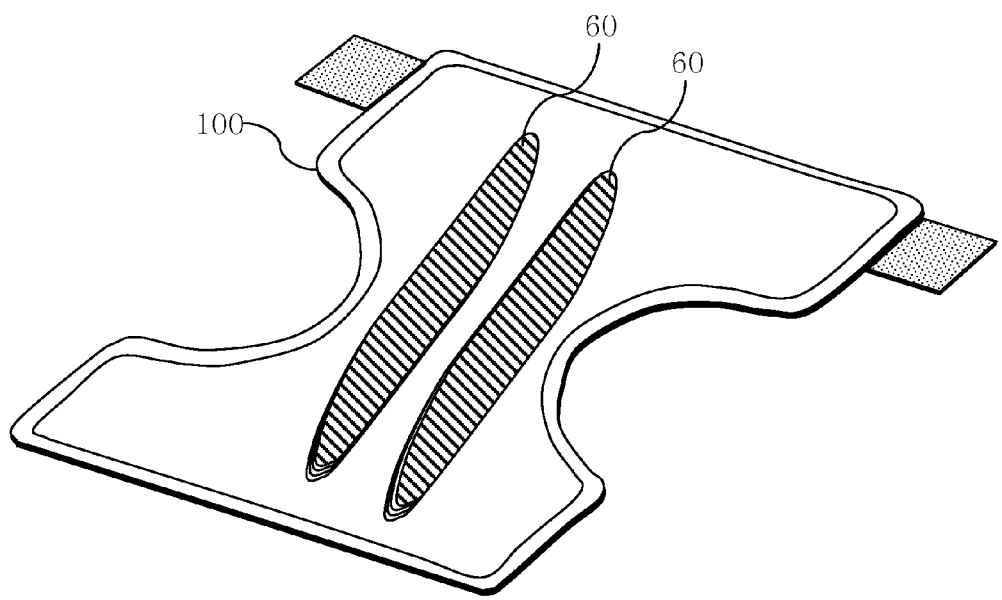
FIG. 13 is a top perspective view of the interior of a diaper having two sensor assemblies thereon in accordance with an aspect of the invention.

Shown in FIG. 13 is a diaper 100 with two sensor assemblies 60 located in the crotch region. This configuration may be advantageously employed in large diapers such as large adult male diapers. In the example shown in FIG. 13, the sensor assemblies 60 are preferably the elongated sensor assembly 60e described in connection with FIG. 11 or the sensor assemblies described in connection with FIG. 14 below.

Figure 14:
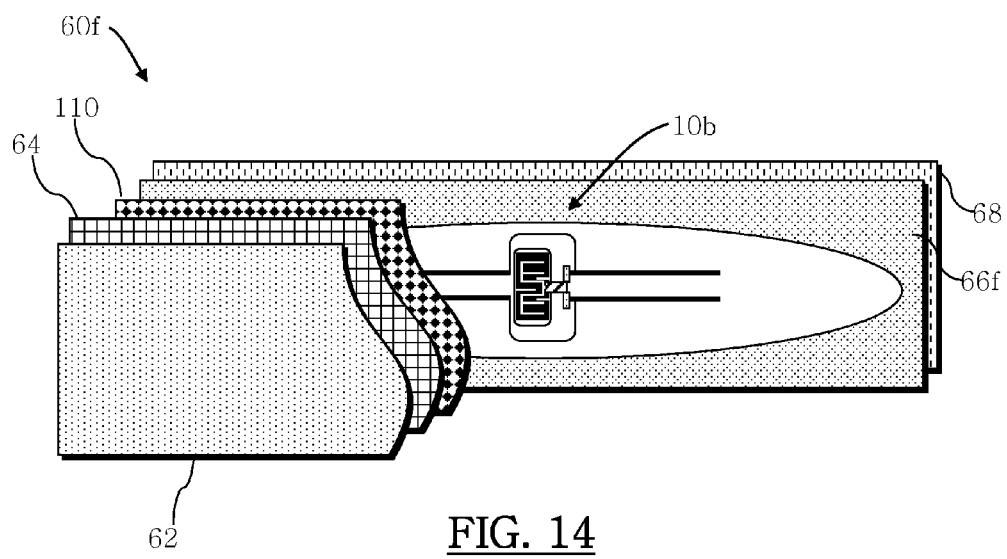
FIG. 14 is a top exploded view of a sixth embodiment of a sensor assembly in accordance with an aspect of the invention, in which the top layer, liquid management layer, and ADL layer are cut-away to provide a better view of the elongated sensor.

FIG. 14 shows an embodiment of the sensor assembly 60f that is particularly useful in this situation because it allows for the wetness sensing area to be very large. In an exemplary embodiment, the wetness sensing area is about 30 cm long and about 10 cm wide. The sensor assembly 60f construction is similar to the embodiment described in connection with FIG. 11 but with an added acquisition and distribution (ADL) layer 110 to control the flow of liquid toward or from the sensor or sensors as desired. The ADL layer 110 is conventionally used in many diaper designs. It is located above the absorbent layer 66f to move liquids to avoid leakage. In those cases where it is desirable to differentiate between an insult coming from the front of the diaper and an insult coming from the back of the diaper, multiple sensors 10b can be used and the ADL layer 110 is helpful in keeping those liquids separated.

C. Wetness Sensor Integrated into Undergarment

Figure 15:
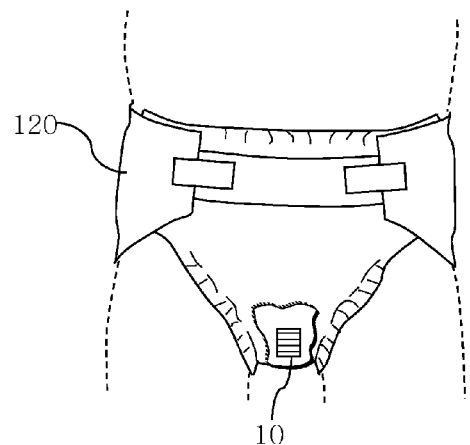
FIG. 15 is a diagram of a person wearing an undergarment in the form of a diaper having a wetness sensor attached thereto in accordance with an aspect of the invention.
Figure 16:
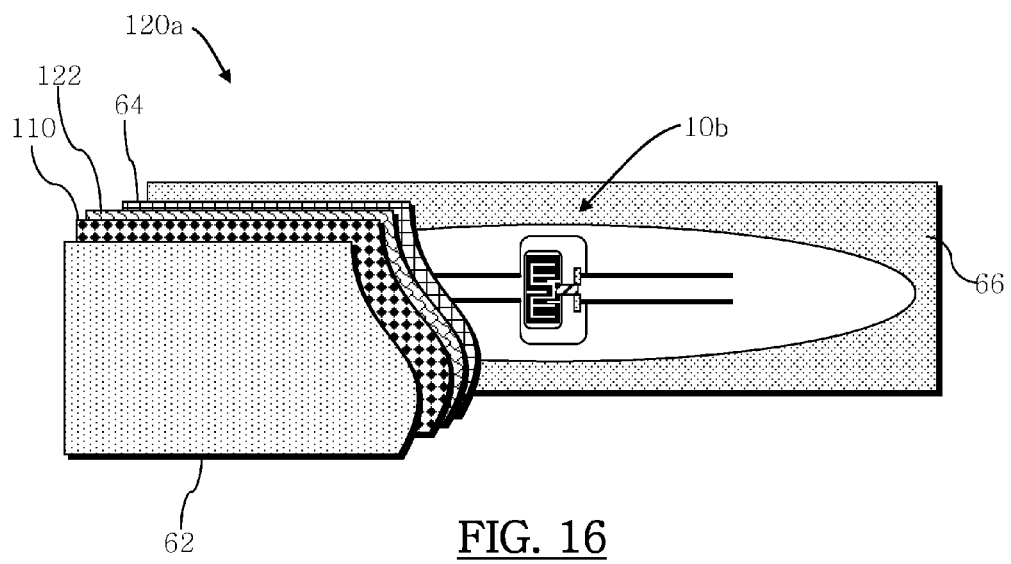
FIG. 16 is a top exploded view of a portion of an undergarment having a sensor assembly installed therein in accordance with an aspect of the invention, in which the top four layers are cut-away to provide a better view of the elongated sensor.

Referring to FIG. 15, another aspect of the invention is a undergarment 120 such as a diaper or brief having one or more sensors 10 integrated therein. A typical example of the undergarment 120 construction, showing how a sensor 10 is integrated therein is best seen in the cut-away view of the undergarment 120a in FIG. 16. The sensor 10 may be any of the sensor embodiments described herein. The undergarment 120a includes a plurality of many of the same material layers described in connection with the sensor assemblies. The undergarment 120a acts like a diaper to direct liquid away from the skin of the user and store it in an absorbent material. In such embodiments, therefore, the sensor 10b is incorporated into the material layers used to make the undergarment 120a. Accordingly, rather than being a undergarment 120a insert like the sensor assemblies, the undergarment 120a has the sensor 10b built in.

The undergarment 120a includes a top layer 62, ADL layer 110, absorbent core 122, fluid management layer 64, sensor 10b, and an absorbent layer 66. The top layer 62 is preferably made of hydrophilic nonwoven polypropylene material. It allows the moisture to proceed through to the underlying layer while giving the user the feeling of dryness. The ADL layer 110 is typically located near the wetness source where urine is most likely to be deposited. The ADL layer 110 is in the form of a patch that spreads and/or moves liquids very quickly into the absorbent 66 layer and reduces the potential for leakage. The use and/or choice of materials used in the ADL layer 110 depends on the materials chosen for the absorbent layer 66. Typical ADL forming materials are resin bonded nonwovens, air bond nonwovens, "curly" fibers found in certain "high loft" configurations like aperture film made of perforated plastic. This layer typically has a blue color when used in current diaper/brief manufacturing.

The absorbent core 122 is preferably made of a cellulosic pulp derived from pine trees or polypropylene-based synthetic fibers. It is often dispersed with super absorbent polymer (SAP) for extra liquid absorption. The thinner the absorbent core 122, the more important the ADL layer 110 becomes for distributing moisture throughout the surface area to avoid clogging of the absorbent core 122. In this arrangement, the sensor 10b is preferably oriented such that the leads 26, 28 directly contact the fluid management layer 64. The substrate 20 is preferably a semi-permeable material designed to intercept small quantities of liquid from getting to the sensor 10b. This eliminates false alert signals due to sweat or minor wetness events. The liquid management layer 64 overlaps the sensor 10b in such a way as to force liquid to move beyond its periphery and into the absorbent layer 66 prior to the liquid coming into contact with the leads 26, 28. The fluid management layer 64, then, controls the speed and quantity of liquid that eventually reaches the leads 26,28.

Figure 17:
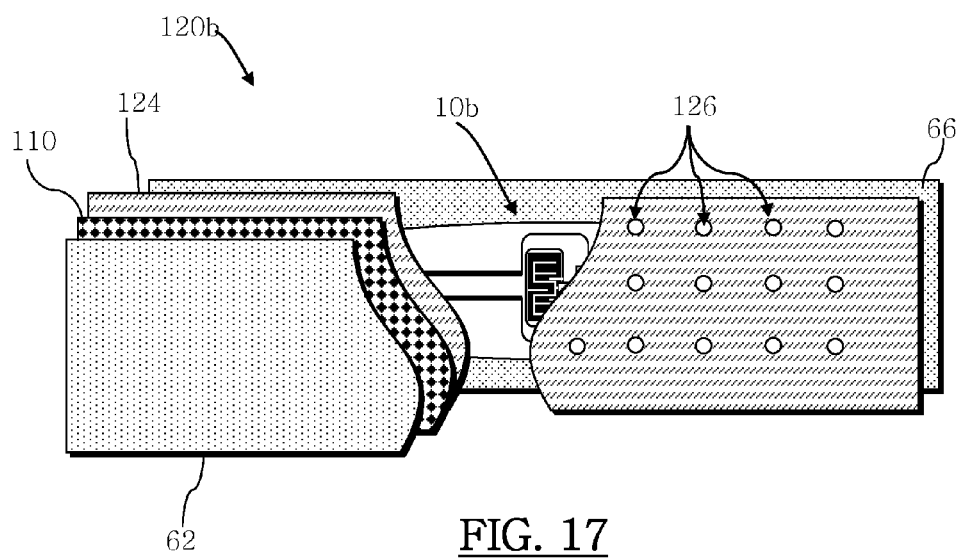
FIG. 17 is a top exploded view of a portion of another undergarment having a sensor assembly installed therein in accordance with an aspect of the invention, in which the top two layers are substantially cut-away to provide a better view of the ADL layer, which is partially cut-away to so that the sensor can be seen.

FIG. 17 is cut-away view of another embodiment of an undergarment 120b configured for those applications where the undergarment 120b will be worn throughout the night, thereby leading to the expectation that the undergarment 120b will be subjected to multiple urine insults. This embodiment includes a mechanism for liquid storage and release, thereby allowing for multiple insults to be monitored from a single sensor. When the undergarment 120b is wetted, the liquid is first stored in one or more liquid retention zones (chambers, etc.) until it can be released into the absorbent layer 66. A sensor 10b is in contact with this liquid retention zone and signals an insult. Once all the fluid is desorbed from the chambers, the sensor 10b stops transmitting signals. Upon rewetting, the sensor 10b once again transmits a wetness event signal. This process is repeated until the sensor 10b is removed from the wetness zone.

The embodiment of the undergarment 120b of FIG. 17 utilizes a number of layers that constitute a fluid storage and release mechanism. It includes a top layer 62, an ADL layer 110, a liquid retention layer 124, a sensor 10b, and an absorbent layer 66. The top layer 62 allows liquid to penetrate, thereby giving the individual the feeling of dryness. The liquid then moves to the ADL layer 110, where it is distributed over a large area to avoid clogging the absorbent layer 66 immediately below the point of liquid incursion. After passing through the ADL layer 110, the liquid penetrates the liquid retention layer 124.

The liquid retention layer 124 is preferably made from plastic film having a plurality of apertures 126 formed therein. The sensor 10b is oriented such that the galvanic cell 24 directly abuts the liquid retention layer 124. The void spaces surrounding the apertures 126 catch large volumes of liquid until the liquid can be absorbed by the absorbent layer 66 located below the sensor 10b. When the liquid contacts the leads 26,28 the galvanic cell 24 generates electricity for sending a wetness alert signal to the detector 14. If the volume of liquid is sufficient, the sensor 10b sends the wetness alert signal. When the liquid is finally absorbed by the absorbent layer 66, the galvanic cell 24 becomes inactive until it is contacted by liquid from a subsequent insult.

To increase the voltage and/or current output of the galvanic cell 24, the concentration of ionic species in the wetting liquid can be increased by incorporating cationic and/or anionic salts into one or more of the material layers of the undergarment or sensor assembly. The cationic salts may include, but are not limited to, Na, K, Al, Fe, Ca, Au, and/or Ag salts. The anionic salts may include, but are not limited to Cl, F, Br, sulfate, phosphate, and/or nitrate salts. In a preferred embodiment, one or more salts are incorporated into the absorbent layer 66 in the vicinity of the sensor 10a,b. In the alternative, the one or more salts are added directly adjacent to the galvanic cell 24 in an adhesive matrix that can become wetted in the presence of liquid.

The sensor 10*a,b* may be built inside a diaper during the diaper manufacturing process. For example, the sensor 10*a,b* may be added to the diaper's impermeable lining or atop the permeable fluid pass-through layer. Excess fluid not absorbed by the absorbent layer may pass onto the permeable layer and into the diapers wetness control system.

Additionally, using new electronic printing technology, the sensor 10*a,b* may be printed onto or into the diaper during diaper manufacturing.

Depending on the size and desired target area for wetness, more than two sensors and/or sensor assemblies may be used.

D. Computer-Based Wetness Monitoring System

The sensors, sensor assemblies, and sensor integrated undergarments described above are particularly useful when employed in a computer based wetness monitoring system. The inventors have developed a computer based wetness monitoring system that may be used by a monitoring agent, such as a caregiver, to monitor the wetness of a child or a patient, for example. A preferred system, in accordance with an aspect of the invention, allows the caregiver to receive an alert signal when a wetness event, such as urination or deification, occurs, thereby allowing the caregiver to respond to the event quickly. As is described in greater detail below, one or more of the wetness sensors are affixed to the item to be monitored in such a position as to allow the one or more sensors to be insulted with the liquid to be detected. A receiver-transmitter (transceiver), assigned to detect electromagnetic signals from the wetness sensor is located within detection range of the RF signal transmitted from the wetness sensor. The transceiver is programmed with information specific to the item being monitored. When a wetness sensor is insulted, the galvanic cell powers the sensor and the sensor subsequently transmits a series of data to the transceiver. The data may include a code specific to the insulted wetness sensor, data representing the state or value received from the sensor, position or orientation information when available, and other data associated with the wetness sensor. The transceiver passes this data along with its identification to a remote database. The system may then be initialized and ready for the next wetness event or can wait until the wetness sensor or monitored device (e.g. diaper) is replaced before reinitialization. The transceiver may be worn by the user and placed remotely from the user.

Figure 18:
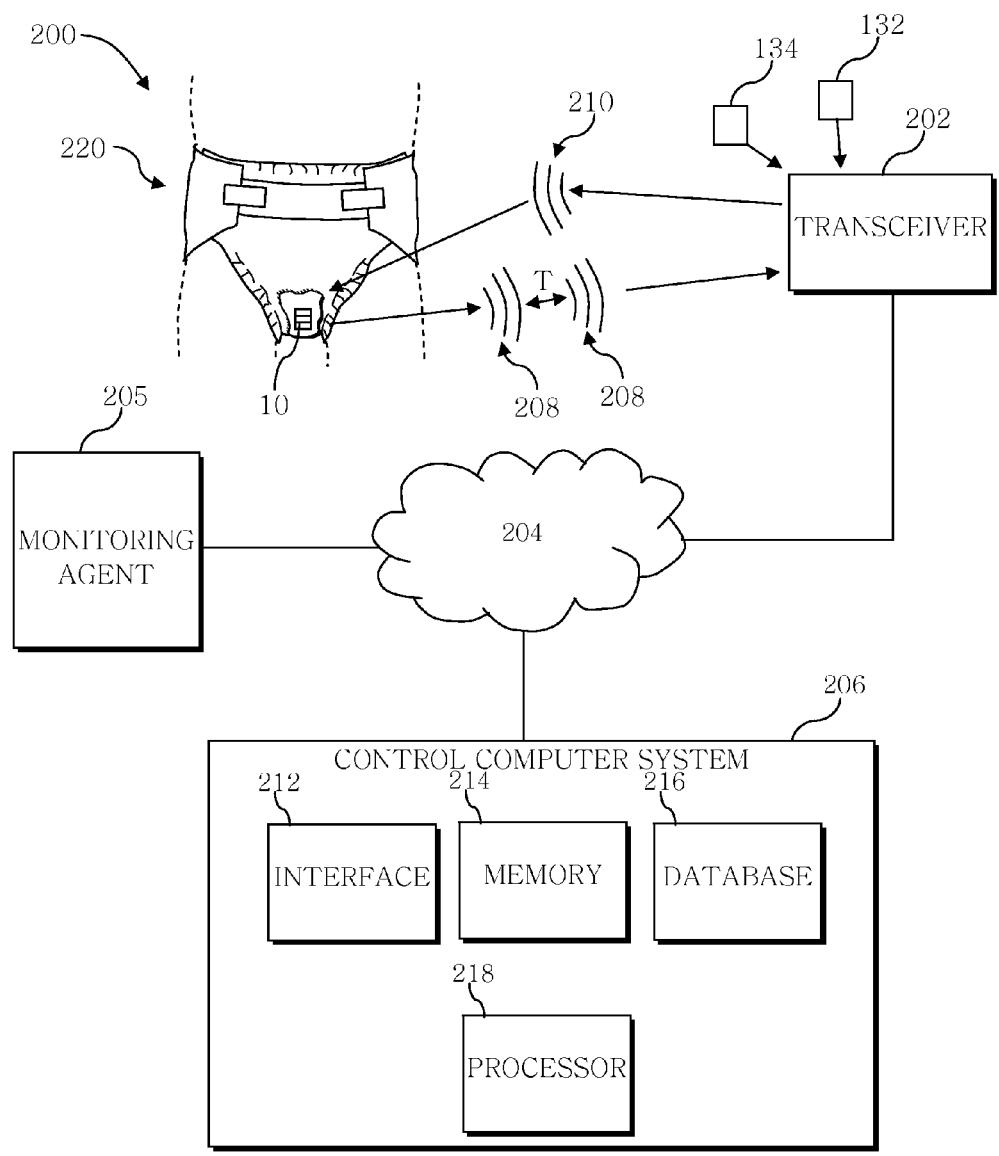
FIG. 18 is schematic of a wetness monitoring system in accordance with an aspect of the invention.

Referring to FIG. 18, a wetness monitoring system 200 in accordance with an aspect of the invention includes a wetness sensor 10, a transceiver 202 and a control computer system 206.

When the sensor 10 detects a wetness event, it generates and transmits data packets 208 separated by a time interval T, containing data about the wetness event to the transceiver 202. The transceiver 202 is also capable of sending a transceiver signal 210 to the sensor 10. In many implementations of the wetness monitoring system 200, the sensor 200 is associated with an undergarment 220 worn by a user.

The transceiver 202 and control computer system 206 are able to communicate data back and forth via a network 204. The network 204 may be an internet network and/or ethernet network, for example.

A monitoring agent 205 is capable of communicating with the control computer system 206 via the network 204. This allows the monitoring agent 205 to receive wetness event alerts from the control computer system 206. Monitoring agents 205 include but are not limited to patient or child caregivers such as medical personnel or parents, and any other party that is interested in receiving an alert when a sensor is activated.

The control computer system 206 includes an interface 212, machine readable memory 214, and database 216. The control computer system 206 and its interface 212 and database 216 are realized by at least one processor 218 executing program instructions stored on the machine readable memory 214. The system 200 is not limited to any particular number, type, or configuration of processors 218, nor to any particular programming language, memory storage format or memory storage medium.

In implementations of the control computer system 206, the wetness monitoring system 200 is not necessarily limited to any geographical location or networking or connection of the processors and/or storage media, provided that the processors and/or storage media are capable of cooperating to execute the interface 212 and database 216. It is not required that the processors and/or storage media be commonly owned or controlled. Additionally, although the database 216 is referred to here as a single database, it is not necessary that it be located on a single memory media unit or at a single physical location. The database 216 may be divided into sub-databases for categorizing information if desired.

The database 216 includes information about the user, such as, for example, the user's identification, vital statistics, and wetness event history. It also includes information transmitted from the sensor 10 to the transceiver 202 regarding wetness events registered by the sensor 10. Data may be entered manually into the database 216 via the interface 212, which is a network connectable electronic device such as a computer, tablet computer, personal data assistant, mobile telephone, or the like.

Figure 19:
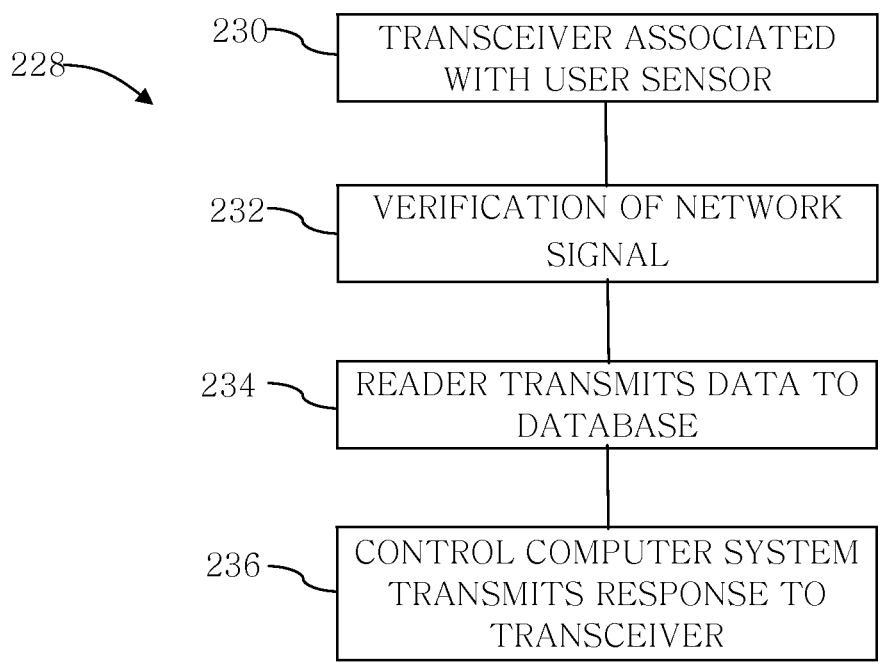
FIG. 19 is a flow diagram of an initialization protocol, which is an aspect of the wetness monitoring system.

Referring to FIG. 19, the system 200 is initiated via an initiation protocol 228. At block 230 the transceiver 202 is associated with a user and a particular sensor 10 or group of sensors being worn by the user. This allows the control computer system 206 to open a user data file in the database 216. Data transmitted from a sensor 10 worn by the user to the transceiver 202 is stored in that particular user's data file.

By way of example, this may implemented in an institutional setting by manually entering information about the user via the interface 212, including the user's identification and room number or location at the institution. The user is then assigned a transceiver 202 configured to communicate with the sensor 10 worn by the user.

At block 232, the transceiver 202 is placed in the user's room and the network connection between the transceiver 202 and database 216 is verified by pressing a button on the transceiver 202.

At block 234 the transceiver 202 communicates data to the database 216 via wireless repeaters placed throughout the institution to detect data transmissions from all of the various transceivers 202 assigned to other users at the institution. The initial data stream from the transceiver 202 to the database 216 reflects that fact that that it is an initialization data transmission. The initial data stream may also report the battery condition of the transceiver 202. At block 236, the control computer system 206 sends an ACK response to the transceiver 202.

An added benefit of placing different transceivers 202 throughout the institution is that, should the user move to a different location in the institution, an alternate transceiver 202 will detect the user's movement and provide a form of user geo-tracking within the institution. When multiple sensors 10 are concurrently transmitting data through a common transceiver or multiple transceiver are operating in close proximity, data transmission is achieved using anti-collision RF protocol.

Figure 20:
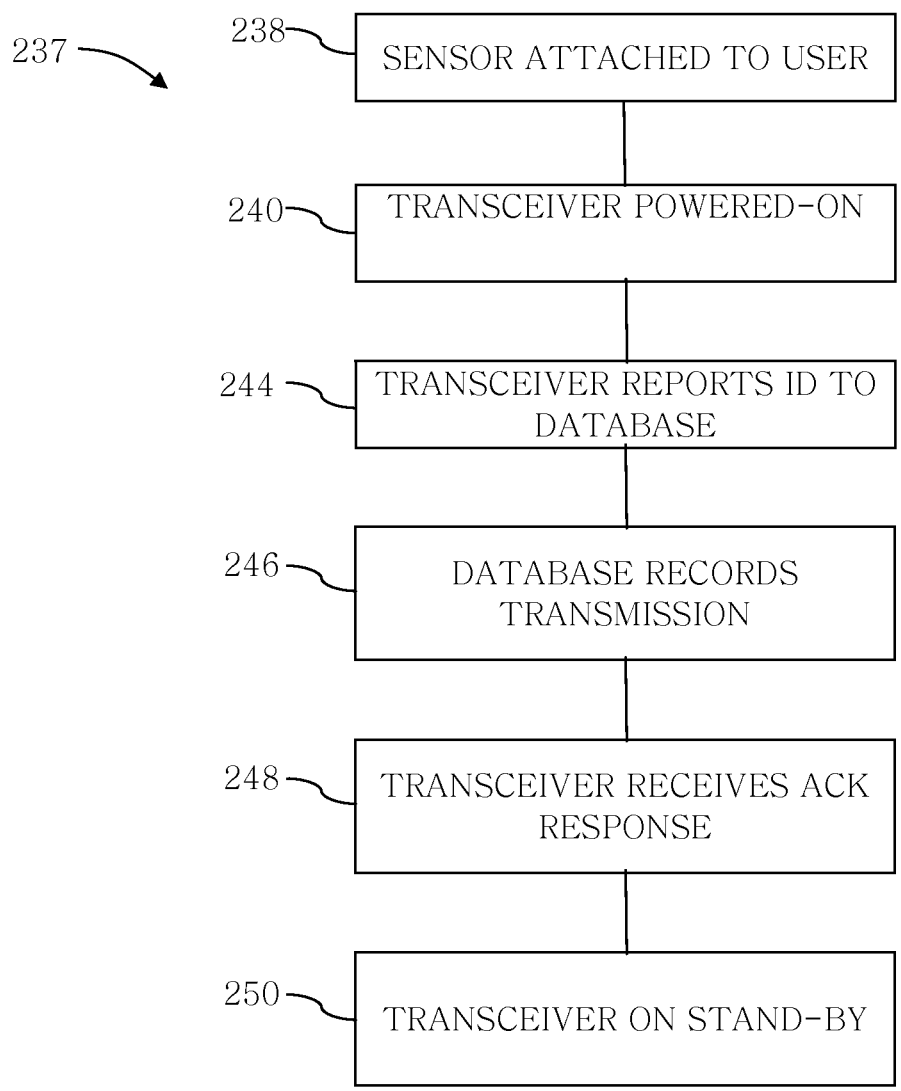
FIG. 20 is a flow diagram of a user preparation protocol, which is an aspect of the wetness monitoring system.

Moving now to FIG. 20, a user preparation protocol 237 in accordance with an aspect of the wetness monitoring system 200 begins at block 238 where the sensor 10 is attached to the user in the form of an individual sensor attached to the user's undergarment 220, a sensor assembly 60 placed in the user's undergarment, or an undergarment 120 having a sensor 10 integrated therein. At block 240, the transceiver is powered-on and begins communication with the database 216. At block 244, the transceiver 202 transmits a transceiver identification signal to the database 216, allowing the control computer system 206 to identify the appropriate user data file. The control computer system 206 subsequently records the identification, date, time, and reason for the transmission in the user data file (block 246) and the transceiver receives an ACK response (block 248). The transceiver 202 then enters stand-by mode while waiting to receive a signal from a sensor 10.

Figure 21:
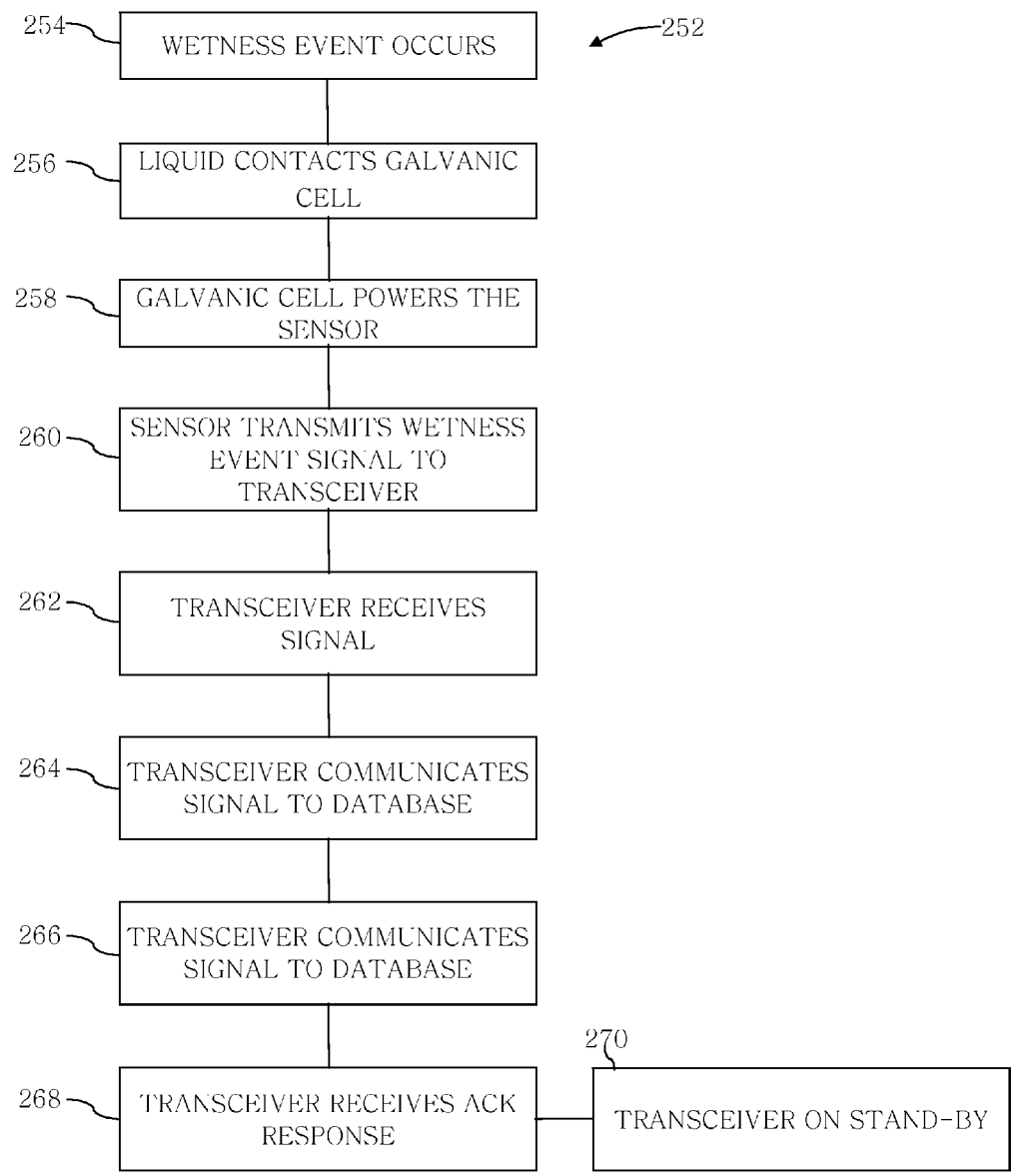
FIG. 21 is a flow diagram of a wetness detection and reporting protocol, which is an aspect of the wetness monitoring system.

FIG. 21 outlines a wetness detection and reporting protocol 252 in accordance with another aspect of the wetness monitoring system 200. When user urinates or defecates, a wetness event occurs (block 254) and the liquid eventually comes in contact with the galvanic cell 24 (block 256), which powers the sensor 10 (block 258). The sensor 10 transmits a wetness event signal to the transceiver 202 (block 260) the transceiver 202 subsequently receives the signal (block 262). The transceiver 202 then communicates the wetness to the database 216 (block 264) and receives an ACK response (block 268) from the control computer system 206, acknowledging that the data was received by the database. 216 Data about the wetness event that is recorded in the database 216 includes the date, time, and information about the wetness event. The transceiver reverts back to stand-by (block 270). If another wetness event occurs, the detection and reporting protocol 252 is repeated.

Figure 22:
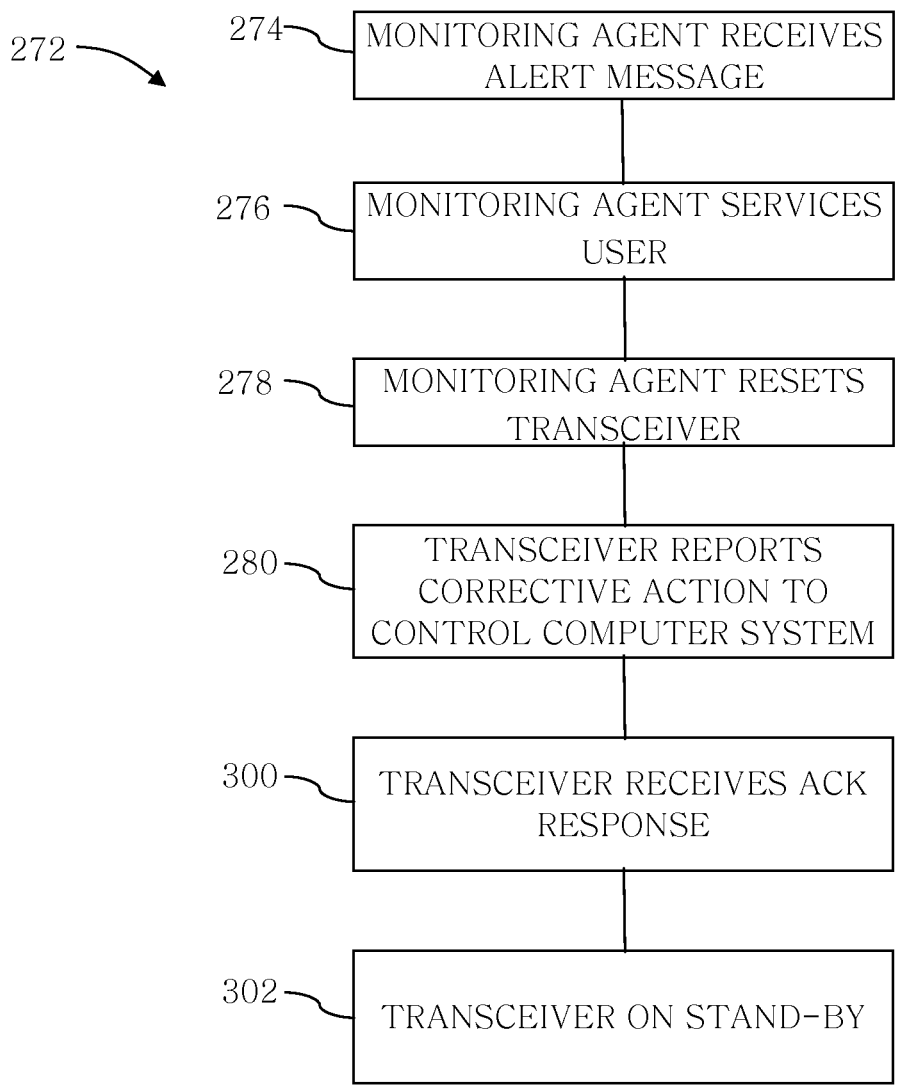
FIG. 22 is a flow diagram of a wetness alert protocol, which is an aspect of the wetness monitoring system.

In accordance with yet another aspect of the wetness monitoring system 200, after a wetness event, the wetness alert protocol 272 in FIG. 22 may be initiated. In the alert protocol 272, one or more monitoring agents receive an alert indicator (block 274). The alert indicator may be in the form of an electronic message such as an email or SMS message sent by the control computer system 206 to the monitoring agent's network connectable electronic device and/or an audible alarm. The monitoring agent may then service the sensor 10 user (block 276) by engaging the user, removing the soiled undergarment, and replacing the soiled undergarment with a new undergarment equipped with a sensor. The monitoring agent then resets the transceiver 202 (block 278) by, for example, pressing a reset button on the transceiver 202. The transceiver 202 subsequently reports to the control computer system 206 that the corrective action was taken (block 280) and receives an ACK response (block 300) from the control computer system 206, acknowledging that the data was received by the database 216. When the new sensor 10 is attached to the user, the system then 200 reverts back to the initiation protocol 228.

The transceiver 202 may be pre-programmed to define the number of wetness events that must occur and/or the number of sensors that must be triggered before an alarm indicator is sent. This allows the monitoring agent to configure their particular application as they choose.

If the transceiver 202 is equipped with a GPS unit 132, accelerometer 134, and/or other electronic component such as a temperature sensor, the transceiver 202 may transmit location, accelerometer, and/or temperature data to the transceiver control computer system 206. Preferably, to avoid false alarms, the transceiver is pre-programmed only to send such data to the control computer system 206, when the data fall outside of certain atypical parameters. When an atypical reading occurs, however, the transceiver 202 transmits a signal to the control computer system 206 indicating the transceiver's 202 identification and reason for the transmission. The transmission is then recorded in the database 216. The control computer system 206 may subsequently send an alert indicator to the monitoring agent.

With respect to the accelerometer 134, because a user will typically move around often during the awake periods and seldomly during sleep, accelerometer 134 movements will become more predictable based on the movement history of the user. When the transceiver 202 is equipped with an accelerometer 134 transmits to the control computer system 206 an atypical movement such as a fall or sudden vibration, the control computer system 206 stores the information transmitted in the user data file. In addition, normal nocturnal movements of the user are typically indicative of normal sleep patterns. When these movements change beyond a pre-defined threshold, it can indicate a problem, unknown to the monitoring agent, that the user is experiencing. Events such as sleepwalking and falling out of bed or continuous movement while in bed can be detected by the accelerometer 134 as an indication of the need for immediate attention.

The database 216 may include one or more predictive algorithms designed to predict a subsequent wetness event based on a user's previous wetness events. In this case, the control computer system 206 may send an alert indicator to the monitoring agent, alerting the monitoring agent of the likelihood of an impending wetness event, giving it the ability to preclude said event by taking corrective action in advance. Predictive algorithms may utilize a variety of information including: subject toileting and wetting history, subject recent activity levels (e.g. sleep, wake, active), recent subject locations (e.g. cafeteria, bed, coffee shop), subject orientation, and subject-specific history and physical information that may be stored in the database 216.

E. Odorant Sensing

In another aspect of the invention the wetness sensor is replaced with an odor sensor. Is this aspect, the arrangement of the previously described sensor assemblies, undergarments with integrated sensors, and the operation of wetness detection system are the same, except for the fact that the signal is transmitted to the detector in response to an odor, rather than wetness. The odorant (a chemical tag added to the wetness absorbing article) may include a number of scented or unscented volatile chemicals, including alcohols, ketones, thiols, esters, etc. The odorant is detected using a chosen sensor, which may be selected from among surface acoustic wave (SAW) sensors, metal-organic semiconductor (MOS) sensors, field effective transisitors (FETs), or chemoresistive sensors. The odorant causes a change in the physical or chemical state of the sensor which can be read and interpreted electrically by the sensor reader. The sensor device may have an odorant filter selective to the given chemical to be detected. The odorant may be chosen among those most unlike odors found in health facilities to prevent false positives.

An odorant that interacts with the chosen insult is first applied to a wetness absorbing article. An external odorant sensor, such as a MOS sensor, is powered and set to detection mode. As fluid is discharged into a wetness absorbing article, the fluid releases (via chemical reaction, dissolving of protective coating, aerosolization, etc.) the odorant gas into the surrounding article space. As the gas escapes from the article, the external sensor is triggered at a predetermined in-air concentration to signal the presence of the insult, indicating that the article must be changed or attended to.

In one embodiment, the odorant comprises alcohols entrapped within a water-dissolvable matrix. As urine passes over the matrix due to an incontinence event, the alcohol is released into the atmosphere. A sensor-transceiver worn by the patient on the diaper is triggered to the active signaling state by the presence of the alcohols in the environs and signals to the detector that a wetness event has occurred.

Decomposition products of urine, such as ammonias, may be chosen as the odorants. Various chemicals that hasten the production of such decomposition products may also be used to increase the concentration of the odorants at the sensor. The decomposition products of urine from biological decomposition factors, such as bacteria, can also be used as the odorant.

The odorants may be incorporated anywhere within an undergarment, such as a diaper, from the back-liner to the top layer. The odorant may be strategically placed within the garment to reflect wetting patterns. In the case of a diaper, should the caregiver desire that only full diapers be changed, the odorant may be placed only at the extremes of the diaper geometry, such as at the waist or along the edges of the article. In this manner, initial fluids will be absorbed in the central absorbent layers of the diaper. As the diaper reaches fullness, fluid will be forced to distribute to the edges of the garment where the odorant resides, thus triggering the odorant sensor and transmitting a wetness event as described herein.

Multiple odorants or taggants may be utilized to determine the location and/or level of saturation of the diaper. This information may be useful in predicting incontinence events since it will provide information each time an incontinence event occurs, along with a relative volume already absorbed in the diaper. Additionally, the quantity of taggants detected at the sensor may provide flow or volume information.

The chemical sensor may also be able to directly detect the odor from the event (urine or fecal matter), breakdown odors, or byproducts of the event interacting with the diaper without the need for a taggants or odorant added to the diaper.

The odorant may cause a physical change outside of typical electronic changes found in many sensors. In one embodiment, the sensor consists of a color/pattern change material and an optical detector. The color change may be from one hue/saturation/value to another or the colors may show up in a pattern that can be read similar to a barcode. The color change material may be in a state of permanence (replaceable), may last for a chosen duration, or may be reversible where the caregiver can reset the color/pattern change via application of voltage, current, chemicals, physical pressure, magnetization, or other means.

The optical detector may be a colorimeter, spectrophotometer, UV-Vis spectroscope, optical imager, pattern detector, barcode scanner, or the like. The optical detector periodically scans the color/pattern change material to conserve battery power. The optical detector may be separate from the wetted article or it may be applied to the article surface. In one embodiment, the optical detector is attached to the back of a disposable article and the color change is measured directly from the article. The monitoring agent is also presented with an optical mechanism of identifying wetness alongside with the electronic mechanism.

F. Sensor in Liquid Collection Bag

The sensor 10a,b may be placed into a liquid collection bag, such as a urine or other waste collection bag, or a fluid supply bags to indicate the presence of fluid in the bag. This can be used to determine when the bag is full or empty. Multiple sensors 10a,b built into the bag can be used to determine the rate of filling or percentage of fullness based on the timing of the firing of the sensors 10a,b. Furthermore, a single sensor 10a,b with a degree of wetness detection mode can also be used.

Figure 23:
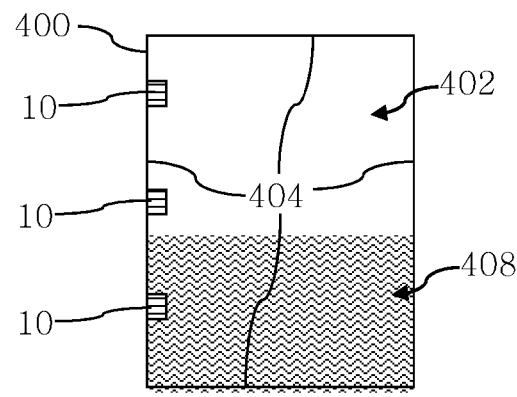
FIG. 23 is a side elevation view of a liquid collection bag including a plurality of wetness sensors for measuring the amount of liquid in the bag in accordance with an aspect of the invention.

Referring to FIG. 23, in accordance with an aspect of the invention, a liquid collection bag 400 includes a bag interior 402 defined by a plurality of bag interior walls 404. Three wetness sensors 10 are vertically spaced apart along one of the interior walls 404 for detecting the level of liquid 408 in the bag 400

The sensor 10a,b configuration implemented into collection bags can make use of the fluid management layer 64 and absorbent layer 66. To avoid wetting the sensor 10a,b from incoming fluid drops or splashes, the fluid management 64 and absorbent layers 66 may take on a number of configurations. In one embodiment, the absorbent layer 66 is a thin membrane that runs the length of the collection bag while the fluid management layer 64 is a sheath that surrounds the sensor. The absorbent layer 66 absorbs sufficient fluid to trigger the sensor 10a,b at a given fluid height in the bag, signaling fullness. Fluid containers for lubricants, hydraulics, as well as blood or IV fluid are of the numerous applications for this concept.

Because the sensors 10a,b are inexpensive and shelf life of the galvanic cell 24 is very long, the sensors 10a,b can be built into the bags and remain inactive until wetted. A transceiver 202 may be attached to a bedside pole or other location to facilitate communication with other electronic devices to indicate problems or maintenance requirements (e.g. replace bag). The transceiver 202 may also be built into an existing monitor, such as an integrated patient monitor like a Philips Intellivue system.

G. Wound Care

Similar to wetness detection in a diaper, detection of moisture in a wound dressing is also important. In another aspect of the invention, one or more of the wetness sensors 10a,b are embedded into or attached to a wound dressing to indicate the presence of moisture or the amount of moisture present under or in the bandage. The sensor 10a,b may communicate with a transceiver 202 that communicates with a database 216 as described above. In the wound care application, differentiation between different fluid types such as blood, sweat, or pus for example, may provide additional information about the status of the wound (e.g. infected, healthy, actively bleeding).

Figure 24:
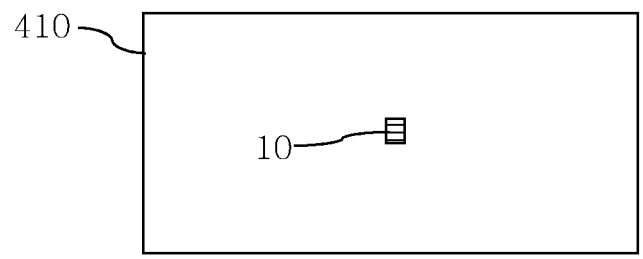
FIG. 24 is a side elevation view of a wound dressing including a wetness sensor in accordance with an aspect of the invention.

Referring to FIG. 24, a wound dressing 410 in accordance with an aspect of the invention, includes a wetness sensor 10 attached thereto.

Ion-selective electrodes that utilizes polymers such as PVC or polyurethane can detect a number of cations and anions. Furthermore, selective enzymatic coatings may be applied to selectively sense diaminobutanes and other chemicals that may signal necrosis due to infection. Such sensors may be worn as a wound dressing or as a simpler test strip.

Pathogenic bacteria or other infectious agents can themselves be sensed through the use of coatings, membranes, or antibody/antigen pathways. Microbial response in such a system is tested by ion transport through a bilayer lipid membrane-coated solid state electrode allows for selectivity and decreased source resistance in the electrode assembly, which is then captured by the sensor electronics and transmitted in the data stream or burst timing. Other embodiments include using biological recognition components such as receptors, nucleic acids, and antibodies with the appropriate transducer. Potentiometric and amperometric designs may also be implemented.

H. Lateral Liquid Flow Test Strip

The wetness sensor 10a,b may be incorporated into a lateral flow test strip or immunoassay to detect the presence of an analyte fluid. This same sensor may be configured to detect and transmit the results of the assay to the transceiver 202 and on to the database 216.

I. Temperature Sensing

Materials with various solid-liquid transition temperatures can be placed on or with the wetness sensor 10a,b to enable temperature sensing. When the material reaches its melting temperature it will turn to liquid which will activate the sensor 10a,b. As describes above, the sensor 10a,b then transmits a signal to the transceiver.

Suitable materials include materials, mixtures, and compounds with adjustable solid-liquid transition temperatures depending on the material composition including can be eutectic, peritectic, or pressure-sensitive phase transition materials.

This aspect of the invention may be used to determine when a box, crate, device, or item exceeds a certain temperature. This may be useful for applications that require very careful temperature control such as food storage, organs for transplant storage, and storage of organic or other samples for testing.

J. Moisture Sensing in Materials or Air

A number of desiccants and other hygroscopic materials absorb humidity. For example, some gels, gelatins, acrylates, and other materials readily absorb moisture. Because the sensors 10a,b function using very low power, this allows the sensor 10a,b to generate a voltage and current even in partially-wetted environments if a conductive path through the hygroscopic material or moisture absorbent material is available.

This is also useful for testing condensation that may accumulate over a period of days. The sensor 10a,b may act as a high humidity sensor, an air leakage sensor, in an airtight container, or for many other purposes.

K. Pressure Sensing

A pressure sensor can be created by augmenting the wetness sensor with a small packet of liquid that is adapted to be released when pressure is applied to the packet. This packet may contain salt water and be made of different materials and construction to optimally trigger the sensor when a desired pressure is achieved.

Additionally, this configuration may be used to activate the sensor "upon demand" by simply squeezing the packet manually or with a mechanical device. The release of the liquid allows the sensor 10a,b to remain wet for many hours, which prolongs the ability of the sensor 10a,b to transmit data to the transceiver 202. For example, the sensor/liquid-packet combination may be placed on surgical sponges for allowing the packet to be broken just before use. The sensor 10a,b on the sponge will transmit data continuously while in use. The sponge may then be placed in a metal container to "silence" the transmission upon removal from the body. Additionally, the liquid may be removed by a second process (either drying, removal, or absorption) thus disabling the sensor 10a,b.

L. Hand Hygiene Monitoring

Another useful application of the sensor 10a,b is in hand hygiene monitoring. In this example, a sensor 10a,b may be placed on the hand, wrist, or finger (like a bandage, wrist strap, or ring). The sensor 10a,b will trigger and send a signal every time the hands come in contact with soap or other fluids. This signal is transmitted to transceivers 202 in various locations (soap dispensers, patient bed receivers, central stations) for monitoring compliance with hand hygiene protocols.

The invention has been described above with reference to preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Accordingly, this invention may be embodied in many different forms and should not be construed as limited to the embodiments set forth herein. Rather, these embodiments are provided so that this disclosure will be thorough, complete, and will fully convey the scope of the invention to those skilled in the art. Therefore, in the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and the appended claims.

That which is claimed is:

1. A liquid sensor, comprising:
   a substrate having a plurality of electrodes, a circuit, and a transmitter thereon;
   the plurality of electrodes being coupled to generate electrical power when in contact with liquid;
   the circuit being electrically connected to the electrodes and configured to:
      be activated by the electrical power,
      detect an electrical parameter of the electrical power, store the electrical power, and
      generate and transmit a plurality of data packets indicating a degree of wetness corresponding to the detected electrical parameter to the transmitter until a pre-determined electrical power value of the stored electrical power is met, wherein successive data packets are separated by a time interval, the time interval being proportional to the time required to reach the pre-determined electrical power; and
   the transmitter being electrically coupled to the circuit and configured to: receive the plurality of data packets and transmit representations of the plurality of data packets as electromagnetic signals.

2. The liquid sensor of claim 1, wherein each successive data packet is separated by a time interval, the time interval being proportional to the detected electrical parameter.

3. The liquid sensor of claim 1, wherein a data packet is generated when the electrical power is released.

4. The liquid sensor of claim 1, wherein the detected electrical parameter is selected from voltage, resistance, current, or a combination thereof.

5. The liquid sensor of claim 1, wherein the degree of wetness corresponds to an amount of liquid in proximity to the electrodes.

6. The liquid sensor of claim 1, wherein the substrate is a flexible electrical insulator and includes a generally planar surface and wherein the plurality of electrodes, circuit, and transmitter are arranged in a co-planar relationship along the generally planar surface.

7. The liquid sensor of claim 1, wherein the substrate is elongated along a lengthwise direction, a first electrode includes a first electrically conductive wire extending along the lengthwise direction and a second electrode includes a second electrically conductive wire extending along the lengthwise direction.

8. The liquid sensor of claim 1, further comprising a plurality of liquid absorbent material layers, the substrate being positioned therebetween.

9. The liquid sensor of claim 1, wherein the liquid sensor is positioned on an undergarment of a user.

10. A method of detecting liquid, the method comprising:
   detecting the presence of liquid in proximity to a sensor, the sensor having a substrate with a plurality of electrodes, a circuit, and a transmitter positioned thereon; the plurality of electrodes being coupled to generate electrical power when in contact with liquid; the circuit being electrically connected to the electrodes and configured to:
      be activated by the electrical power,
      detect an electrical parameter of the electrical power,
      store the electrical power,
      generate and transmit a plurality of data packets indicating a degree of wetness corresponding to the detected electrical parameter to the transmitter until a pre-determined electrical power value of the stored electrical power is met, wherein successive data packets are separated by a time interval, the time interval being proportional to the time required to reach the pre-determined electrical power; and
   receiving a transmitted signal from the sensor, the signal including representations of the plurality of data packets.

11. The method of claim 10, further comprising:
   determining an amount of liquid in proximity to the electrodes by correlating the detected electrical parameter with a wetness value.

12. The method of claim 10, further comprising:
   determining a type of liquid in proximity to the electrodes by correlating the detected electrical parameter with a liquid type.

13. A wetness detection system, comprising:
   a wetness sensor comprising:
      a substrate having a plurality of electrodes, a circuit, and a transmitter thereon;
      the plurality of electrodes being coupled to generate electrical power when in contact with liquid;
      the circuit being electrically connected to the electrodes and configured to:
      be activated by the electrical power,
      detect an electrical parameter of the electrical power,
      store the electrical power,
      generate and transmit a plurality of data packets indicating a degree of wetness corresponding to the detected electrical parameter to the transmitter until a pre-determined electrical power value of the stored electrical power is met, wherein successive data packets are separated by a time interval, the time interval being proportional to the time required to reach the pre-determined electrical power;
      the transmitter being electrically coupled to the circuit and configured to: receive the plurality of data packets and transmit representations of the plurality of data packets as electromagnetic signals; and
   one or more transceivers adapted to receive the plurality of data packets and communicate data over a communication network to an electronic database.

14. The wetness detection system of claim 13, further comprising a computer processor configured to execute machine readable program instructions to alert a monitoring agent when wetness is sensed.

15. The wetness detection system of claim 13, wherein a wetness event occurs when liquid contacts the electrodes, and the system further comprises a computer processor configured to execute machine readable program instructions to predict future wetness events of a sensor user based on wetness event history data stored on the database for that sensor user.

* * * * *